US009714434B2

(12) United States Patent
Cosset et al.

(10) Patent No.: US 9,714,434 B2
(45) Date of Patent: *Jul. 25, 2017

(54) VECTOR PARTICLES FOR TARGETING CD34+ CELLS

(71) Applicant: INSTITUT NATIONAL DE LA SANTE ET DE LA RECHERCHE MEDICALE (INSERM), Paris (FR)

(72) Inventors: Francois-Loic Cosset, Lyons (FR); Els Verhoeyen, Lyons (FR); Caroline Costa, Lyons (FR); Cecilia Frecha, Lyons (FR)

(73) Assignee: INSTITUT NATIONAL DE LA SANTE ET DE LA RECHERCHE MEDICALE (INSERM), Paris (FR)

( * ) Notice: Subject to any disclaimer, the term of this patent is extended or adjusted under 35 U.S.C. 154(b) by 192 days.

This patent is subject to a terminal disclaimer.

(21) Appl. No.: 13/913,815

(22) Filed: Jun. 10, 2013

(65) Prior Publication Data

US 2014/0017792 A1    Jan. 16, 2014

Related U.S. Application Data

(63) Continuation of application No. 12/670,479, filed as application No. PCT/EP2008/059674 on Jul. 23, 2008, now Pat. No. 8,557,573.

(30) Foreign Application Priority Data

Jul. 23, 2007 (EP) ..................... 07290918

(51) Int. Cl.
*C12N 15/00* (2006.01)
*C07K 14/15* (2006.01)
*C12N 15/86* (2006.01)
*A61K 48/00* (2006.01)

(52) U.S. Cl.
CPC .............. *C12N 15/86* (2013.01); *A61K 48/00* (2013.01); *C07K 2319/02* (2013.01); *C07K 2319/42* (2013.01); *C12N 2740/16043* (2013.01); *C12N 2740/16045* (2013.01); *C12N 2810/6045* (2013.01); *C12N 2810/852* (2013.01)

(58) Field of Classification Search
None
See application file for complete search history.

(56) References Cited

U.S. PATENT DOCUMENTS 8,338,168 B2   12/2012  Trono et al.
2014/0017792 A1*  1/2014  Cosset ............... C12N 15/86
                                                    435/456

OTHER PUBLICATIONS

Jiing-Kuan Yee, et al., "Generation of High-Titer Pseudotyped Retroviral Vectors with Very Broad Host Range", 1994, pp. 99-112, vol. 43, Methods in Cell Biology.
Els Verhoeyen, et al., "Novel Lentiviral Vectors Displaying "Early-Acting Cytokines" Selectively Promote Survival and Transduction of NOD/SCID repopulating Human Hematopoietic Stem Cells", Nov. 15, 2005, pp. 3386-3395, vol. 106, No. 10, Blood.
D. Ott, et al., "Sequence Analysis of Amphotropic and 10A1 Murine Leukemia Viruses: Close Relationship to Mink Cell Focus-Inducing Viruses", Feb. 1990, pp. 757-766, vol. 64, No. 2, Journal of Virology.
Theodora Hatziioannou, et al., "Incorporation of Fowl Plague Virus Hemagglutinin into Murine Leukemia Virus Particles and Analysis of the Infectivity of the Pseudotype Retroviruses", Jun. 1998, pp. 5313-5317, vol. 72, No. 6, Journal of Virology.
Luigi Naldini, et al., "Lentiviral Vectors", 2000, pp. 599-609, vol. 55, Advances in Virus Research.
Virginie Sandrin, et al., "Lentiviral Vectors Pseudotyped with a modified RD114 Envelope Glycoprotein Show Increased Stability in Sera and Augmented Transduction of Primary Lymphocytes and CD34 + Cells Derived from Human and Nonhuman Primates", Aug. 1, 2002, pp. 823-832, vol. 100, No. 3 Blood.
François-Loïc Cosset, et al., "High-Titer Packaging Cells Producing Recombinant Retroviruses Resistant to Human Serum" Dec. 1995, pp. 7430-7436, vol. 69, No. 12, Journal of Virology.
Julie Bayle, et al., " Suppressor of Cytokine Signaling 6 Associates with KIT and Regulates KIT Receptor Signaling*" Issue of Mar. 26, 2004, pp. 12249-12259, vol. 279, No. 13, The Journal of Biological Chemistry.
Didier Nègre, et al., "Vectors Derived from Simian Immunodeficiency Virus (SIV)", 2002, pp. 1161-1171, vol. 84, Biochimie.
Amy E. Geddis, et al., "Phosphatidylinositol 3-Kinase is Necessary but not Sufficient for Thrombopoietin-induced Proliferation in Engineered Mpl-bearing Cell Lines as Well as in Primary Megakaryocytic Progenitors", Issue of Sep. 14, 2001, pp. 34473-34479, vol. 276, No. 37, The Journal of Biological Chemistry.
Leonie K. Ashman, "The Biology of Stem Cell Factor and its Receptor C-kit", 1999, pp. 1037-1051, vol. 31, The International Journal of Biochemistry & Cell Biology.

* cited by examiner

Primary Examiner — Michael Burkhart
(74) Attorney, Agent, or Firm — B. Aaron Schulman, Esq.; Stites & Harbison, PLLC.

(57) ABSTRACT

The present invention relates to a vector particle for transferring biological material into cells, wherein said vector particle comprises at least:
a first protein which comprises the transmembrane and extracellular domains of the feline endogenous RD114 virus envelope glycoprotein, and
a second protein which comprises a ligand of the c-Kit receptor.

15 Claims, 4 Drawing Sheets

SEQUENCE LISTING

<160> NUMBER OF SEQ ID NOS: 15

<210> SEQ ID NO 1
<211> LENGTH: 1692
<212> TYPE: DNA
<213> ORGANISM: Artificial sequence
<220> FEATURE:
<223> OTHER INFORMATION: Fusion of the transmembrane and extracellular
      domains of the feline endogenous RD114 virus envelope glycoprotein
      and the cytoplasmic domain of MLV-A envelope glycoprotein
<220> FEATURE:
<221> NAME/KEY: CDS
<222> LOCATION: (1)..(1692)

<400> SEQUENCE: 1

```
atg aaa ctc cca aca gga atg gtc att tta tgt agc cta ata ata gtt      48
Met Lys Leu Pro Thr Gly Met Val Ile Leu Cys Ser Leu Ile Ile Val
1               5                   10                  15
```

-continued

| | |
|---|---|
| cgg gca ggg ttt gac gac ccc cgc aag gct atc gca tta gta caa aaa<br>Arg Ala Gly Phe Asp Asp Pro Arg Lys Ala Ile Ala Leu Val Gln Lys<br>20              25              30 | 96 |
| caa cat ggt aaa cca tgc gaa tgc agc gga ggg cag gta tcc gag gcc<br>Gln His Gly Lys Pro Cys Glu Cys Ser Gly Gly Gln Val Ser Glu Ala<br>35              40              45 | 144 |
| cca ccg aac tcc atc caa cag gta act tgc cca ggc aag acg gcc tac<br>Pro Pro Asn Ser Ile Gln Gln Val Thr Cys Pro Gly Lys Thr Ala Tyr<br>50              55              60 | 192 |
| tta atg acc aac caa aaa tgg aaa tgc aga gtc act cca aaa atc tca<br>Leu Met Thr Asn Gln Lys Trp Lys Cys Arg Val Thr Pro Lys Ile Ser<br>65          70              75              80 | 240 |
| cct agc ggg gga gaa ctc cag aac tgc ccc tgt aac act ttc cag gac<br>Pro Ser Gly Gly Glu Leu Gln Asn Cys Pro Cys Asn Thr Phe Gln Asp<br>85              90              95 | 288 |
| tcg atg cac agt tct tgt tat act gaa tac cgg caa tgc agg cga att<br>Ser Met His Ser Ser Cys Tyr Thr Glu Tyr Arg Gln Cys Arg Arg Ile<br>100             105             110 | 336 |
| aat aag aca tac tac acg gcc acc ttg ctt aaa ata cgg tct ggg agc<br>Asn Lys Thr Tyr Tyr Thr Ala Thr Leu Leu Lys Ile Arg Ser Gly Ser<br>115             120             125 | 384 |
| ctc aac gag gta cag ata tta caa aac ccc aat cag ctc cta cag tcc<br>Leu Asn Glu Val Gln Ile Leu Gln Asn Pro Asn Gln Leu Leu Gln Ser<br>130             135             140 | 432 |
| cct tgt agg ggc tct ata aat cag ccc gtt tgc tgg agt gcc aca gcc<br>Pro Cys Arg Gly Ser Ile Asn Gln Pro Val Cys Trp Ser Ala Thr Ala<br>145             150             155             160 | 480 |
| ccc atc cat atc tcc gat ggt gga gga ccc ctc gat act aag aga gtg<br>Pro Ile His Ile Ser Asp Gly Gly Gly Pro Leu Asp Thr Lys Arg Val<br>165             170             175 | 528 |
| tgg aca gtc caa aaa agg cta gaa caa att cat aag gct atg act cct<br>Trp Thr Val Gln Lys Arg Leu Glu Gln Ile His Lys Ala Met Thr Pro<br>180             185             190 | 576 |
| gaa ctt caa tac cac ccc tta gcc ctg ccc aaa gtc aga gat gac ctt<br>Glu Leu Gln Tyr His Pro Leu Ala Leu Pro Lys Val Arg Asp Asp Leu<br>195             200             205 | 624 |
| agc ctt gat gca cgg act ttt gat atc ctg aat acc act ttt agg tta<br>Ser Leu Asp Ala Arg Thr Phe Asp Ile Leu Asn Thr Thr Phe Arg Leu<br>210             215             220 | 672 |
| ctc cag atg tcc aat ttt agc ctt gcc caa gat tgt tgg ctc tgt tta<br>Leu Gln Met Ser Asn Phe Ser Leu Ala Gln Asp Cys Trp Leu Cys Leu<br>225             230             235             240 | 720 |
| aaa cta ggt acc cct acc cct ctt gcg ata ccc act ccc tct tta acc<br>Lys Leu Gly Thr Pro Thr Pro Leu Ala Ile Pro Thr Pro Ser Leu Thr<br>245             250             255 | 768 |
| tac tcc cta gca gac tcc cta gcg aat gcc tcc tgt cag att ata cct<br>Tyr Ser Leu Ala Asp Ser Leu Ala Asn Ala Ser Cys Gln Ile Ile Pro<br>260             265             270 | 816 |
| ccc ctc ttg gtt caa ccg atg cag ttc tcc aac tcg tcc tgt tta tct<br>Pro Leu Leu Val Gln Pro Met Gln Phe Ser Asn Ser Ser Cys Leu Ser<br>275             280             285 | 864 |
| tcc cct ttc att aac gat acg gaa caa ata gac tta ggt gca gtc acc<br>Ser Pro Phe Ile Asn Asp Thr Glu Gln Ile Asp Leu Gly Ala Val Thr<br>290             295             300 | 912 |
| ttt act aac tgc acc tct gta gcc aat gtc agt agt cct tta tgt gcc<br>Phe Thr Asn Cys Thr Ser Val Ala Asn Val Ser Ser Pro Leu Cys Ala<br>305             310             315             320 | 960 |
| cta aac ggg tca gtc ttc ctc tgt gga aat aac atg gca tac acc tat<br>Leu Asn Gly Ser Val Phe Leu Cys Gly Asn Asn Met Ala Tyr Thr Tyr<br>325             330             335 | 1008 |

-continued

```
tta ccc caa aac tgg acc aga ctt tgc gtc caa gct tcc ctc ctc ccc      1056
Leu Pro Gln Asn Trp Thr Arg Leu Cys Val Gln Ala Ser Leu Leu Pro
        340                 345                 350 gac att gac atc aac ccg ggg gat gag cca gtc ccc att cct gcc att      1104
Asp Ile Asp Ile Asn Pro Gly Asp Glu Pro Val Pro Ile Pro Ala Ile
355                 360                 365 gat cat tat ata cat aga cct aaa cga gct gta cag ttc atc cct tta      1152
Asp His Tyr Ile His Arg Pro Lys Arg Ala Val Gln Phe Ile Pro Leu
        370                 375                 380 cta gct gga ctg gga atc acc gca gca ttc acc acc gga gct aca ggc      1200
Leu Ala Gly Leu Gly Ile Thr Ala Ala Phe Thr Thr Gly Ala Thr Gly
385                 390                 395                 400 cta ggt gtc tcc gtc acc cag tat aca aaa tta tcc cat cag tta ata      1248
Leu Gly Val Ser Val Thr Gln Tyr Thr Lys Leu Ser His Gln Leu Ile
                405                 410                 415 tct gat gtc caa gtc tta tcc ggt acc ata caa gat tta caa gac cag      1296
Ser Asp Val Gln Val Leu Ser Gly Thr Ile Gln Asp Leu Gln Asp Gln
            420                 425                 430 gta gac tcg tta gct gaa gta gtt ctc caa aat agg agg gga ctg gac      1344
Val Asp Ser Leu Ala Glu Val Val Leu Gln Asn Arg Arg Gly Leu Asp
        435                 440                 445 cta cta acg gca gaa caa gga gga att tgt tta gcc tta caa gaa aaa      1392
Leu Leu Thr Ala Glu Gln Gly Gly Ile Cys Leu Ala Leu Gln Glu Lys
    450                 455                 460 tgc tgt ttt tat gct aac aag tca gga att gtg aga aac aaa ata aga      1440
Cys Cys Phe Tyr Ala Asn Lys Ser Gly Ile Val Arg Asn Lys Ile Arg
465                 470                 475                 480 acc cta caa gaa gaa tta caa aaa cgc agg gaa agc ctg gca tcc aac      1488
Thr Leu Gln Glu Glu Leu Gln Lys Arg Arg Glu Ser Leu Ala Ser Asn
                485                 490                 495 cct ctc tgg acc ggg ctg cag ggc ttt ctt ccg tac ctc cta cct ctc      1536
Pro Leu Trp Thr Gly Leu Gln Gly Phe Leu Pro Tyr Leu Leu Pro Leu
            500                 505                 510 ctg gga ccc cta ctc acc ctc ctc ata cta acc att ggg cca tgc          1584
Leu Gly Pro Leu Leu Thr Leu Leu Ile Leu Thr Ile Gly Pro Cys
        515                 520                 525 gtt ttc aat cga tta gtt caa ttt gtt aaa gac agg atc tca gta gtc      1632
Val Phe Asn Arg Leu Val Gln Phe Val Lys Asp Arg Ile Ser Val Val
    530                 535                 540 cag gct tta gtc ctg act caa caa tac cac cag cta aaa cca cta gaa      1680
Gln Ala Leu Val Leu Thr Gln Gln Tyr His Gln Leu Lys Pro Leu Glu
545                 550                 555                 560 tac gag ccg tga                                                      1692
Tyr Glu Pro
```

<210> SEQ ID NO 2
<211> LENGTH: 563
<212> TYPE: PRT
<213> ORGANISM: Artificial sequence
<220> FEATURE:
<223> OTHER INFORMATION: Fusion of the transmembrane and extracellular
      domains of the feline endogenous RD114 virus envelope glycoprotein
      and the cytoplasmic domain of MLV-A envelope glycoprotein

<400> SEQUENCE: 2

Met Lys Leu Pro Thr Gly Met Val Ile Leu Cys Ser Leu Ile Ile Val
1               5                   10                  15

Arg Ala Gly Phe Asp Asp Pro Arg Lys Ala Ile Ala Leu Val Gln Lys
            20                  25                  30

Gln His Gly Lys Pro Cys Glu Cys Ser Gly Gly Gln Val Ser Glu Ala

```
                35                  40                  45
Pro Pro Asn Ser Ile Gln Gln Val Thr Cys Pro Gly Lys Thr Ala Tyr
 50                  55                  60

Leu Met Thr Asn Gln Lys Trp Lys Cys Arg Val Thr Pro Lys Ile Ser
 65                  70                  75                  80

Pro Ser Gly Gly Glu Leu Gln Asn Cys Pro Cys Asn Thr Phe Gln Asp
                 85                  90                  95

Ser Met His Ser Ser Cys Tyr Thr Glu Tyr Arg Gln Cys Arg Arg Ile
                100                 105                 110

Asn Lys Thr Tyr Tyr Thr Ala Thr Leu Leu Lys Ile Arg Ser Gly Ser
            115                 120                 125

Leu Asn Glu Val Gln Ile Leu Gln Asn Pro Asn Gln Leu Leu Gln Ser
        130                 135                 140

Pro Cys Arg Gly Ser Ile Asn Gln Pro Val Cys Trp Ser Ala Thr Ala
145                 150                 155                 160

Pro Ile His Ile Ser Asp Gly Gly Pro Leu Asp Thr Lys Arg Val
                165                 170                 175

Trp Thr Val Gln Lys Arg Leu Glu Gln Ile His Lys Ala Met Thr Pro
                180                 185                 190

Glu Leu Gln Tyr His Pro Leu Ala Leu Pro Lys Val Arg Asp Asp Leu
            195                 200                 205

Ser Leu Asp Ala Arg Thr Phe Asp Ile Leu Asn Thr Thr Phe Arg Leu
        210                 215                 220

Leu Gln Met Ser Asn Phe Ser Leu Ala Gln Asp Cys Trp Leu Cys Leu
225                 230                 235                 240

Lys Leu Gly Thr Pro Thr Pro Leu Ala Ile Pro Thr Pro Ser Leu Thr
                245                 250                 255

Tyr Ser Leu Ala Asp Ser Leu Ala Asn Ala Ser Cys Gln Ile Ile Pro
            260                 265                 270

Pro Leu Leu Val Gln Pro Met Gln Phe Ser Asn Ser Ser Cys Leu Ser
        275                 280                 285

Ser Pro Phe Ile Asn Asp Thr Glu Gln Ile Asp Leu Gly Ala Val Thr
290                 295                 300

Phe Thr Asn Cys Thr Ser Val Ala Asn Val Ser Ser Pro Leu Cys Ala
305                 310                 315                 320

Leu Asn Gly Ser Val Phe Leu Cys Gly Asn Asn Met Ala Tyr Thr Tyr
                325                 330                 335

Leu Pro Gln Asn Trp Thr Arg Leu Cys Val Gln Ala Ser Leu Leu Pro
            340                 345                 350

Asp Ile Asp Ile Asn Pro Gly Asp Glu Pro Val Pro Ile Pro Ala Ile
        355                 360                 365

Asp His Tyr Ile His Arg Pro Lys Arg Ala Val Gln Phe Ile Pro Leu
    370                 375                 380

Leu Ala Gly Leu Gly Ile Thr Ala Ala Phe Thr Thr Gly Ala Thr Gly
385                 390                 395                 400

Leu Gly Val Ser Val Thr Gln Tyr Thr Lys Leu Ser His Gln Leu Ile
                405                 410                 415

Ser Asp Val Gln Val Leu Ser Gly Thr Ile Gln Asp Leu Gln Asp Gln
            420                 425                 430

Val Asp Ser Leu Ala Glu Val Val Leu Gln Asn Arg Arg Gly Leu Asp
        435                 440                 445

Leu Leu Thr Ala Glu Gln Gly Gly Ile Cys Leu Ala Leu Gln Glu Lys
450                 455                 460
```

```
Cys Cys Phe Tyr Ala Asn Lys Ser Gly Ile Val Arg Asn Lys Ile Arg
465                 470                 475                 480

Thr Leu Gln Glu Glu Leu Gln Lys Arg Arg Glu Ser Leu Ala Ser Asn
            485                 490                 495

Pro Leu Trp Thr Gly Leu Gln Gly Phe Leu Pro Tyr Leu Leu Pro Leu
            500                 505                 510

Leu Gly Pro Leu Leu Thr Leu Leu Ile Leu Thr Ile Gly Pro Cys
        515                 520                 525

Val Phe Asn Arg Leu Val Gln Phe Val Lys Asp Arg Ile Ser Val Val
    530                 535                 540

Gln Ala Leu Val Leu Thr Gln Gln Tyr His Gln Leu Lys Pro Leu Glu
545                 550                 555                 560

Tyr Glu Pro

<210> SEQ ID NO 3
<211> LENGTH: 2385
<212> TYPE: DNA
<213> ORGANISM: Artificial sequence
<220> FEATURE:
<223> OTHER INFORMATION: Fusion of the SCF cytokine, the N-terminal
      domain of an influenza virus hemagglutinin glycoprotein, and a
      signal peptide
<220> FEATURE:
<221> NAME/KEY: CDS
<222> LOCATION: (1)..(2385)

<400> SEQUENCE: 3 atg gcg cgt tca acg ctc tca aaa ccc ctt aaa aat aag gtt aac ccg      48
Met Ala Arg Ser Thr Leu Ser Lys Pro Leu Lys Asn Lys Val Asn Pro
1               5                   10                  15 cga ggc ccc cta atc ccc tta att ctt ctg atg ctc aga ggg gtc agt      96
Arg Gly Pro Leu Ile Pro Leu Ile Leu Leu Met Leu Arg Gly Val Ser
                20                  25                  30 act gct tcg ccc ggc tcc agt gcg gcc cag ccg gcc gaa ggg atc tgc     144
Thr Ala Ser Pro Gly Ser Ser Ala Ala Gln Pro Ala Glu Gly Ile Cys
            35                  40                  45 agg aat cgt gtg act aat aat gta aaa gac gtc act aaa ttg gtg gca     192
Arg Asn Arg Val Thr Asn Asn Val Lys Asp Val Thr Lys Leu Val Ala
        50                  55                  60 aat ctt cca aaa gac tac atg ata acc ctc aaa tat gtc ccc ggg atg     240
Asn Leu Pro Lys Asp Tyr Met Ile Thr Leu Lys Tyr Val Pro Gly Met
65                  70                  75                  80 gat gtt ttg cca agt cat tgt tgg ata agc gag atg gta gta caa ttg     288
Asp Val Leu Pro Ser His Cys Trp Ile Ser Glu Met Val Val Gln Leu
                85                  90                  95 tca gac agc ttg act gat ctt ctg gac aag ttt tca aat att tct gaa     336
Ser Asp Ser Leu Thr Asp Leu Leu Asp Lys Phe Ser Asn Ile Ser Glu
            100                 105                 110 ggc ttg agt aat tat tcc atc ata gac aaa ctt gtg aat ata gtc gat     384
Gly Leu Ser Asn Tyr Ser Ile Ile Asp Lys Leu Val Asn Ile Val Asp
        115                 120                 125 gac ctt gtg gag tgc gtc aaa gaa aac tca tct aag gat cta aaa aaa     432
Asp Leu Val Glu Cys Val Lys Glu Asn Ser Ser Lys Asp Leu Lys Lys
    130                 135                 140 tca ttc aag agc cca gaa ccc agg ctc ttt act cct gaa gaa ttc ttt     480
Ser Phe Lys Ser Pro Glu Pro Arg Leu Phe Thr Pro Glu Glu Phe Phe
145                 150                 155                 160 aga att ttt aat aga tcc att gat gcc ttc aag gac ttt gta gtg gca     528
Arg Ile Phe Asn Arg Ser Ile Asp Ala Phe Lys Asp Phe Val Val Ala
                165                 170                 175
```

| | | | | | | | | | | | | | | | | |
|---|---|---|---|---|---|---|---|---|---|---|---|---|---|---|---|---|
| tct | gaa | act | agt | gat | tgt | gtg | gtt | tct | tca | aca | tta | agt | cct | gag | aaa | 576 |
| Ser | Glu | Thr | Ser | Asp | Cys | Val | Val | Ser | Ser | Thr | Leu | Ser | Pro | Glu | Lys | |
| | | | 180 | | | | | 185 | | | | | 190 | | | |
| gat | tcc | aga | gtc | agt | gtc | aca | aaa | cca | ttt | atg | tta | ccc | cct | gtt | gca | 624 |
| Asp | Ser | Arg | Val | Ser | Val | Thr | Lys | Pro | Phe | Met | Leu | Pro | Pro | Val | Ala | |
| | | 195 | | | | | 200 | | | | | 205 | | | | |
| gcc | agc | tcc | ctt | agg | aat | gac | agc | agt | agt | aat | agg | aag | gcc | aaa | | 672 |
| Ala | Ser | Ser | Leu | Arg | Asn | Asp | Ser | Ser | Ser | Asn | Arg | Lys | Ala | Lys | | |
| | | 210 | | | | | 215 | | | | | 220 | | | | |
| aat | ccc | cct | gga | gac | tcc | agc | cta | cac | gcg | gcc | gca | atc | gag | gga | agg | 720 |
| Asn | Pro | Pro | Gly | Asp | Ser | Ser | Leu | His | Ala | Ala | Ala | Ile | Glu | Gly | Arg | |
| 225 | | | | | 230 | | | | | 235 | | | | | 240 | |
| caa | gac | ctt | cca | gga | aat | gac | aac | agc | gac | aaa | att | tgt | ctt | gga | cat | 768 |
| Gln | Asp | Leu | Pro | Gly | Asn | Asp | Asn | Ser | Asp | Lys | Ile | Cys | Leu | Gly | His | |
| | | | | 245 | | | | | 250 | | | | | 255 | | |
| cat | gct | gta | tca | aat | ggc | acc | aaa | gta | aac | aca | ctc | act | gag | aga | gga | 816 |
| His | Ala | Val | Ser | Asn | Gly | Thr | Lys | Val | Asn | Thr | Leu | Thr | Glu | Arg | Gly | |
| | | | 260 | | | | | 265 | | | | | 270 | | | |
| gta | gaa | gtt | gtc | aat | gca | acg | gaa | aca | gtg | gag | cgg | aca | aac | atc | ccc | 864 |
| Val | Glu | Val | Val | Asn | Ala | Thr | Glu | Thr | Val | Glu | Arg | Thr | Asn | Ile | Pro | |
| | | 275 | | | | | 280 | | | | | 285 | | | | |
| aaa | att | tgc | tca | aaa | ggg | aaa | aga | acc | act | gat | ctt | ggc | caa | tgc | gga | 912 |
| Lys | Ile | Cys | Ser | Lys | Gly | Lys | Arg | Thr | Thr | Asp | Leu | Gly | Gln | Cys | Gly | |
| | 290 | | | | | 295 | | | | | 300 | | | | | |
| ctg | tta | ggg | acc | att | acc | gga | cca | cct | caa | tgc | gac | caa | ttt | cta | gaa | 960 |
| Leu | Leu | Gly | Thr | Ile | Thr | Gly | Pro | Pro | Gln | Cys | Asp | Gln | Phe | Leu | Glu | |
| 305 | | | | | 310 | | | | | 315 | | | | | 320 | |
| ttt | tca | gct | gat | cta | ata | atc | gag | aga | cga | gaa | gga | aat | gat | gtt | tgt | 1008 |
| Phe | Ser | Ala | Asp | Leu | Ile | Ile | Glu | Arg | Arg | Glu | Gly | Asn | Asp | Val | Cys | |
| | | | | 325 | | | | | 330 | | | | | 335 | | |
| tac | ccg | ggg | aag | ttt | gtt | aat | gaa | gag | gca | ttg | cga | caa | atc | ctc | aga | 1056 |
| Tyr | Pro | Gly | Lys | Phe | Val | Asn | Glu | Glu | Ala | Leu | Arg | Gln | Ile | Leu | Arg | |
| | | | 340 | | | | | 345 | | | | | 350 | | | |
| gga | tca | ggt | ggg | att | gac | aaa | gaa | aca | atg | gga | ttc | aca | tat | agt | gga | 1104 |
| Gly | Ser | Gly | Gly | Ile | Asp | Lys | Glu | Thr | Met | Gly | Phe | Thr | Tyr | Ser | Gly | |
| | | 355 | | | | | 360 | | | | | 365 | | | | |
| ata | agg | acc | aac | gga | aca | act | agt | gca | tgt | aga | aga | tca | ggg | tct | tca | 1152 |
| Ile | Arg | Thr | Asn | Gly | Thr | Thr | Ser | Ala | Cys | Arg | Arg | Ser | Gly | Ser | Ser | |
| | 370 | | | | | 375 | | | | | 380 | | | | | |
| ttc | tat | gca | gaa | atg | gag | tgg | ctc | ctg | tca | aat | aca | gac | aat | gct | tct | 1200 |
| Phe | Tyr | Ala | Glu | Met | Glu | Trp | Leu | Leu | Ser | Asn | Thr | Asp | Asn | Ala | Ser | |
| 385 | | | | | 390 | | | | | 395 | | | | | 400 | |
| ttc | cca | caa | atg | aca | aaa | tca | tac | aaa | aac | aca | agg | aga | gaa | tca | gct | 1248 |
| Phe | Pro | Gln | Met | Thr | Lys | Ser | Tyr | Lys | Asn | Thr | Arg | Arg | Glu | Ser | Ala | |
| | | | | 405 | | | | | 410 | | | | | 415 | | |
| ctg | ata | gta | tgg | gga | atc | cac | cat | tca | gga | tca | acc | acc | gaa | cag | acc | 1296 |
| Leu | Ile | Val | Trp | Gly | Ile | His | His | Ser | Gly | Ser | Thr | Thr | Glu | Gln | Thr | |
| | | | 420 | | | | | 425 | | | | | 430 | | | |
| aaa | cta | tat | ggg | agt | gga | aat | aaa | ctg | ata | aca | gtc | ggg | agt | tcc | aaa | 1344 |
| Lys | Leu | Tyr | Gly | Ser | Gly | Asn | Lys | Leu | Ile | Thr | Val | Gly | Ser | Ser | Lys | |
| | | 435 | | | | | 440 | | | | | 445 | | | | |
| tat | cat | caa | tct | ttt | gtg | ccg | agt | cca | gga | aca | cga | ccg | cag | ata | aat | 1392 |
| Tyr | His | Gln | Ser | Phe | Val | Pro | Ser | Pro | Gly | Thr | Arg | Pro | Gln | Ile | Asn | |
| | 450 | | | | | 455 | | | | | 460 | | | | | |
| ggc | cag | tcc | gga | cgg | att | gat | ttt | cat | tgg | ttg | atc | ttg | gat | ccc | aat | 1440 |
| Gly | Gln | Ser | Gly | Arg | Ile | Asp | Phe | His | Trp | Leu | Ile | Leu | Asp | Pro | Asn | |
| 465 | | | | | 470 | | | | | 475 | | | | | 480 | |
| gat | aca | gtt | act | ttt | agt | ttc | aat | ggg | gct | ttc | ata | gct | cca | aat | cgt | 1488 |
| Asp | Thr | Val | Thr | Phe | Ser | Phe | Asn | Gly | Ala | Phe | Ile | Ala | Pro | Asn | Arg | |

-continued

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 485 |     |     |     |     | 490 |     |     |     |     | 495 |     |      |
| gcc | agc | ttc | ttg | agg | gga | aag | tcc | atg | ggg | atc | cag | agc | gat | gtg | cag | 1536 |
| Ala | Ser | Phe | Leu | Arg | Gly | Lys | Ser | Met | Gly | Ile | Gln | Ser | Asp | Val | Gln |      |
|     |     |     | 500 |     |     |     |     | 505 |     |     |     |     | 510 |     |     |      |
| gtt | gat | gcc | aat | tgc | gaa | ggg | gaa | tgc | tac | cac | agt | gga | ggg | act | ata | 1584 |
| Val | Asp | Ala | Asn | Cys | Glu | Gly | Glu | Cys | Tyr | His | Ser | Gly | Gly | Thr | Ile |      |
|     |     |     | 515 |     |     |     |     | 520 |     |     |     |     | 525 |     |     |      |
| aca | agc | aga | ttg | cct | ttt | caa | aac | atc | aat | agc | aga | gca | gtt | ggc | aaa | 1632 |
| Thr | Ser | Arg | Leu | Pro | Phe | Gln | Asn | Ile | Asn | Ser | Arg | Ala | Val | Gly | Lys |      |
|     |     | 530 |     |     |     |     | 535 |     |     |     |     | 540 |     |     |     |      |
| tgc | cca | aga | tat | gta | aaa | cag | gaa | agt | tta | tta | ttg | gca | act | ggg | atg | 1680 |
| Cys | Pro | Arg | Tyr | Val | Lys | Gln | Glu | Ser | Leu | Leu | Leu | Ala | Thr | Gly | Met |      |
| 545 |     |     |     |     | 550 |     |     |     |     | 555 |     |     |     |     | 560 |      |
| aag | aac | gtt | ccc | gaa | cct | tcc | aaa | aaa | agg | aaa | aaa | aga | ggc | ctg | ttt | 1728 |
| Lys | Asn | Val | Pro | Glu | Pro | Ser | Lys | Lys | Arg | Lys | Lys | Arg | Gly | Leu | Phe |      |
|     |     |     |     | 565 |     |     |     |     | 570 |     |     |     |     | 575 |     |      |
| ggc | gct | ata | gca | ggg | ttt | att | gaa | aat | ggt | tgg | gaa | ggt | ctg | gtc | gac | 1776 |
| Gly | Ala | Ile | Ala | Gly | Phe | Ile | Glu | Asn | Gly | Trp | Glu | Gly | Leu | Val | Asp |      |
|     |     |     | 580 |     |     |     |     | 585 |     |     |     |     | 590 |     |     |      |
| ggg | tgg | tac | ggt | ttc | agg | cat | cag | aat | gca | caa | gga | gaa | gga | act | gca | 1824 |
| Gly | Trp | Tyr | Gly | Phe | Arg | His | Gln | Asn | Ala | Gln | Gly | Glu | Gly | Thr | Ala |      |
|     |     |     | 595 |     |     |     |     | 600 |     |     |     |     | 605 |     |     |      |
| gca | gac | tac | aaa | agc | acc | caa | tcg | gca | att | gat | cag | ata | acc | gga | aag | 1872 |
| Ala | Asp | Tyr | Lys | Ser | Thr | Gln | Ser | Ala | Ile | Asp | Gln | Ile | Thr | Gly | Lys |      |
|     |     |     | 610 |     |     |     |     | 615 |     |     |     |     | 620 |     |     |      |
| tta | aat | aga | ctc | att | gag | aaa | acc | aac | cag | caa | ttt | gag | cta | ata | gat | 1920 |
| Leu | Asn | Arg | Leu | Ile | Glu | Lys | Thr | Asn | Gln | Gln | Phe | Glu | Leu | Ile | Asp |      |
| 625 |     |     |     |     | 630 |     |     |     |     | 635 |     |     |     |     | 640 |      |
| aat | gaa | ttc | act | gag | gtg | gaa | aag | cag | att | ggc | aat | tta | att | aac | tgg | 1968 |
| Asn | Glu | Phe | Thr | Glu | Val | Glu | Lys | Gln | Ile | Gly | Asn | Leu | Ile | Asn | Trp |      |
|     |     |     |     | 645 |     |     |     |     | 650 |     |     |     |     | 655 |     |      |
| acc | aaa | gac | tcc | atc | aca | gaa | gta | tgg | tct | tac | aat | gct | gaa | ctt | att | 2016 |
| Thr | Lys | Asp | Ser | Ile | Thr | Glu | Val | Trp | Ser | Tyr | Asn | Ala | Glu | Leu | Ile |      |
|     |     |     | 660 |     |     |     |     | 665 |     |     |     |     | 670 |     |     |      |
| gtg | gca | atg | gaa | aac | cag | cac | act | att | gat | ttg | gct | gat | tca | gag | atg | 2064 |
| Val | Ala | Met | Glu | Asn | Gln | His | Thr | Ile | Asp | Leu | Ala | Asp | Ser | Glu | Met |      |
|     |     |     | 675 |     |     |     |     | 680 |     |     |     |     | 685 |     |     |      |
| aac | agg | ctg | tat | gag | cga | gtg | agg | aaa | caa | tta | agg | gaa | aat | gct | gaa | 2112 |
| Asn | Arg | Leu | Tyr | Glu | Arg | Val | Arg | Lys | Gln | Leu | Arg | Glu | Asn | Ala | Glu |      |
|     |     |     | 690 |     |     |     |     | 695 |     |     |     |     | 700 |     |     |      |
| gag | gat | ggt | act | ggt | tgc | ttt | gaa | att | ttt | cat | aaa | tgt | gac | gat | gat | 2160 |
| Glu | Asp | Gly | Thr | Gly | Cys | Phe | Glu | Ile | Phe | His | Lys | Cys | Asp | Asp | Asp |      |
| 705 |     |     |     |     | 710 |     |     |     |     | 715 |     |     |     |     | 720 |      |
| tgt | atg | gct | agt | ata | agg | aac | aat | act | tat | gat | cac | agc | aaa | tac | aga | 2208 |
| Cys | Met | Ala | Ser | Ile | Arg | Asn | Asn | Thr | Tyr | Asp | His | Ser | Lys | Tyr | Arg |      |
|     |     |     |     | 725 |     |     |     |     | 730 |     |     |     |     | 735 |     |      |
| gaa | gaa | gcg | atg | caa | aat | aga | ata | caa | att | gac | cca | gtc | aaa | ttg | agt | 2256 |
| Glu | Glu | Ala | Met | Gln | Asn | Arg | Ile | Gln | Ile | Asp | Pro | Val | Lys | Leu | Ser |      |
|     |     |     | 740 |     |     |     |     | 745 |     |     |     |     | 750 |     |     |      |
| agt | ggc | tac | aaa | gat | gtg | ata | ctt | tgg | ttt | agc | ttc | ggg | gca | tca | tgc | 2304 |
| Ser | Gly | Tyr | Lys | Asp | Val | Ile | Leu | Trp | Phe | Ser | Phe | Gly | Ala | Ser | Cys |      |
|     |     | 755 |     |     |     |     | 760 |     |     |     |     | 765 |     |     |     |      |
| ttt | ttg | ctt | ctt | gcc | att | gca | atg | ggc | ctt | gtt | ttc | ata | tgt | gtg | aag | 2352 |
| Phe | Leu | Leu | Leu | Ala | Ile | Ala | Met | Gly | Leu | Val | Phe | Ile | Cys | Val | Lys |      |
|     |     |     | 770 |     |     |     |     | 775 |     |     |     |     | 780 |     |     |      |
| aac | gga | aac | atg | cgg | tgc | act | att | tgt | ata | taa |     |     |     |     |     | 2385 |
| Asn | Gly | Asn | Met | Arg | Cys | Thr | Ile | Cys | Ile |     |     |     |     |     |     |      |
| 785 |     |     |     |     | 790 |     |     |     |     |     |     |     |     |     |     |      |

```
<210> SEQ ID NO 4
<211> LENGTH: 794
<212> TYPE: PRT
<213> ORGANISM: Artificial sequence
<220> FEATURE:
<223> OTHER INFORMATION: Fusion of the SCF cytokine, the N-terminal
      domain of an influenza virus hemagglutinin glycoprotein, and a
      signal peptide

<400> SEQUENCE: 4
```

Met Ala Arg Ser Thr Leu Ser Lys Pro Leu Lys Asn Lys Val Asn Pro
1               5                   10                  15

Arg Gly Pro Leu Ile Pro Leu Ile Leu Leu Met Leu Arg Gly Val Ser
            20                  25                  30

Thr Ala Ser Pro Gly Ser Ser Ala Ala Gln Pro Ala Glu Gly Ile Cys
        35                  40                  45

Arg Asn Arg Val Thr Asn Asn Val Lys Asp Val Thr Lys Leu Val Ala
50                  55                  60

Asn Leu Pro Lys Asp Tyr Met Ile Thr Leu Lys Tyr Val Pro Gly Met
65                  70                  75                  80

Asp Val Leu Pro Ser His Cys Trp Ile Ser Glu Met Val Val Gln Leu
                85                  90                  95

Ser Asp Ser Leu Thr Asp Leu Leu Asp Lys Phe Ser Asn Ile Ser Glu
            100                 105                 110

Gly Leu Ser Asn Tyr Ser Ile Ile Asp Lys Leu Val Asn Ile Val Asp
        115                 120                 125

Asp Leu Val Glu Cys Val Lys Glu Asn Ser Ser Lys Asp Leu Lys Lys
130                 135                 140

Ser Phe Lys Ser Pro Glu Pro Arg Leu Phe Thr Pro Glu Glu Phe Phe
145                 150                 155                 160

Arg Ile Phe Asn Arg Ser Ile Asp Ala Phe Lys Asp Phe Val Val Ala
                165                 170                 175

Ser Glu Thr Ser Asp Cys Val Val Ser Ser Thr Leu Ser Pro Glu Lys
            180                 185                 190

Asp Ser Arg Val Ser Val Thr Lys Pro Phe Met Leu Pro Pro Val Ala
        195                 200                 205

Ala Ser Ser Leu Arg Asn Asp Ser Ser Ser Ser Asn Arg Lys Ala Lys
210                 215                 220

Asn Pro Pro Gly Asp Ser Ser Leu His Ala Ala Ala Ile Glu Gly Arg
225                 230                 235                 240

Gln Asp Leu Pro Gly Asn Asp Asn Ser Asp Lys Ile Cys Leu Gly His
                245                 250                 255

His Ala Val Ser Asn Gly Thr Lys Val Asn Thr Leu Thr Glu Arg Gly
            260                 265                 270

Val Glu Val Val Asn Ala Thr Glu Thr Val Glu Arg Thr Asn Ile Pro
        275                 280                 285

Lys Ile Cys Ser Lys Gly Lys Arg Thr Thr Asp Leu Gly Gln Cys Gly
290                 295                 300

Leu Leu Gly Thr Ile Thr Gly Pro Pro Gln Cys Asp Gln Phe Leu Glu
305                 310                 315                 320

Phe Ser Ala Asp Leu Ile Ile Glu Arg Arg Glu Gly Asn Asp Val Cys
                325                 330                 335

Tyr Pro Gly Lys Phe Val Asn Glu Glu Ala Leu Arg Gln Ile Leu Arg
            340                 345                 350

Gly Ser Gly Gly Ile Asp Lys Glu Thr Met Gly Phe Thr Tyr Ser Gly
        355                 360                 365

```
Ile Arg Thr Asn Gly Thr Thr Ser Ala Cys Arg Arg Ser Gly Ser Ser
    370                 375                 380

Phe Tyr Ala Glu Met Glu Trp Leu Leu Ser Asn Thr Asp Asn Ala Ser
385                 390                 395                 400

Phe Pro Gln Met Thr Lys Ser Tyr Lys Asn Thr Arg Arg Glu Ser Ala
                405                 410                 415

Leu Ile Val Trp Gly Ile His His Ser Gly Ser Thr Thr Glu Gln Thr
                420                 425                 430

Lys Leu Tyr Gly Ser Gly Asn Lys Leu Ile Thr Val Gly Ser Ser Lys
            435                 440                 445

Tyr His Gln Ser Phe Val Pro Ser Pro Gly Thr Arg Pro Gln Ile Asn
        450                 455                 460

Gly Gln Ser Gly Arg Ile Asp Phe His Trp Leu Ile Leu Asp Pro Asn
465                 470                 475                 480

Asp Thr Val Thr Phe Ser Phe Asn Gly Ala Phe Ile Ala Pro Asn Arg
                485                 490                 495

Ala Ser Phe Leu Arg Gly Lys Ser Met Gly Ile Gln Ser Asp Val Gln
            500                 505                 510

Val Asp Ala Asn Cys Glu Gly Glu Cys Tyr His Ser Gly Gly Thr Ile
        515                 520                 525

Thr Ser Arg Leu Pro Phe Gln Asn Ile Asn Ser Arg Ala Val Gly Lys
    530                 535                 540

Cys Pro Arg Tyr Val Lys Gln Glu Ser Leu Leu Leu Ala Thr Gly Met
545                 550                 555                 560

Lys Asn Val Pro Glu Pro Ser Lys Lys Arg Lys Lys Arg Gly Leu Phe
                565                 570                 575

Gly Ala Ile Ala Gly Phe Ile Glu Asn Gly Trp Glu Gly Leu Val Asp
            580                 585                 590

Gly Trp Tyr Gly Phe Arg His Gln Asn Ala Gln Gly Glu Gly Thr Ala
        595                 600                 605

Ala Asp Tyr Lys Ser Thr Gln Ser Ala Ile Asp Gln Ile Thr Gly Lys
        610                 615                 620

Leu Asn Arg Leu Ile Glu Lys Thr Asn Gln Gln Phe Glu Leu Ile Asp
625                 630                 635                 640

Asn Glu Phe Thr Glu Val Glu Lys Gln Ile Gly Asn Leu Ile Asn Trp
                645                 650                 655

Thr Lys Asp Ser Ile Thr Glu Val Trp Ser Tyr Asn Ala Glu Leu Ile
            660                 665                 670

Val Ala Met Glu Asn Gln His Thr Ile Asp Leu Ala Asp Ser Glu Met
        675                 680                 685

Asn Arg Leu Tyr Glu Arg Val Arg Lys Gln Leu Arg Glu Asn Ala Glu
    690                 695                 700

Glu Asp Gly Thr Gly Cys Phe Glu Ile Phe His Lys Cys Asp Asp Asp
705                 710                 715                 720

Cys Met Ala Ser Ile Arg Asn Asn Thr Tyr Asp His Ser Lys Tyr Arg
                725                 730                 735

Glu Glu Ala Met Gln Asn Arg Ile Gln Ile Asp Pro Val Lys Leu Ser
            740                 745                 750

Ser Gly Tyr Lys Asp Val Ile Leu Trp Phe Ser Phe Gly Ala Ser Cys
        755                 760                 765

Phe Leu Leu Leu Ala Ile Ala Met Gly Leu Val Phe Ile Cys Val Lys
    770                 775                 780
```

```
Asn Gly Asn Met Arg Cys Thr Ile Cys Ile
785                 790
```

<210> SEQ ID NO 5
<211> LENGTH: 530
<212> TYPE: PRT
<213> ORGANISM: Artificial sequence
<220> FEATURE:
<223> OTHER INFORMATION: Transmembrane and extracellular domains of the
      feline endogenous RD114 virus envelope glycoprotein

<400> SEQUENCE: 5

```
Met Lys Leu Pro Thr Gly Met Val Ile Leu Cys Ser Leu Ile Val
1               5                   10                  15

Arg Ala Gly Phe Asp Asp Pro Arg Lys Ala Ile Ala Leu Val Gln Lys
            20                  25                  30

Gln His Gly Lys Pro Cys Glu Cys Ser Gly Gln Val Ser Glu Ala
            35                  40                  45

Pro Pro Asn Ser Ile Gln Gln Val Thr Cys Pro Gly Lys Thr Ala Tyr
50                  55                  60

Leu Met Thr Asn Gln Lys Trp Lys Cys Arg Val Thr Pro Lys Ile Ser
65                  70                  75                  80

Pro Ser Gly Gly Glu Leu Gln Asn Cys Pro Cys Asn Thr Phe Gln Asp
                85                  90                  95

Ser Met His Ser Ser Cys Tyr Thr Glu Tyr Arg Gln Cys Arg Arg Ile
            100                 105                 110

Asn Lys Thr Tyr Tyr Thr Ala Thr Leu Leu Lys Ile Arg Ser Gly Ser
            115                 120                 125

Leu Asn Glu Val Gln Ile Leu Gln Asn Pro Asn Gln Leu Leu Gln Ser
130                 135                 140

Pro Cys Arg Gly Ser Ile Asn Gln Pro Val Cys Trp Ser Ala Thr Ala
145                 150                 155                 160

Pro Ile His Ile Ser Asp Gly Gly Pro Leu Asp Thr Lys Arg Val
                165                 170                 175

Trp Thr Val Gln Lys Arg Leu Glu Gln Ile His Lys Ala Met Thr Pro
            180                 185                 190

Glu Leu Gln Tyr His Pro Leu Ala Leu Pro Lys Val Arg Asp Asp Leu
            195                 200                 205

Ser Leu Asp Ala Arg Thr Phe Asp Ile Leu Asn Thr Thr Phe Arg Leu
210                 215                 220

Leu Gln Met Ser Asn Phe Ser Leu Ala Gln Asp Cys Trp Leu Cys Leu
225                 230                 235                 240

Lys Leu Gly Thr Pro Thr Pro Leu Ala Ile Pro Thr Pro Ser Leu Thr
                245                 250                 255

Tyr Ser Leu Ala Asp Ser Leu Ala Asn Ala Ser Cys Gln Ile Ile Pro
            260                 265                 270

Pro Leu Leu Val Gln Pro Met Gln Phe Ser Asn Ser Ser Cys Leu Ser
            275                 280                 285

Ser Pro Phe Ile Asn Asp Thr Glu Gln Ile Asp Leu Gly Ala Val Thr
290                 295                 300

Phe Thr Asn Cys Thr Ser Val Ala Asn Val Ser Ser Pro Leu Cys Ala
305                 310                 315                 320

Leu Asn Gly Ser Val Phe Leu Cys Gly Asn Asn Met Ala Tyr Thr Tyr
                325                 330                 335

Leu Pro Gln Asn Trp Thr Arg Leu Cys Val Gln Ala Ser Leu Leu Pro
            340                 345                 350
```

-continued

```
Asp Ile Asp Ile Asn Pro Gly Asp Glu Pro Val Pro Ile Pro Ala Ile
            355                 360                 365
Asp His Tyr Ile His Arg Pro Lys Arg Ala Val Gln Phe Ile Pro Leu
        370                 375                 380
Leu Ala Gly Leu Gly Ile Thr Ala Ala Phe Thr Thr Gly Ala Thr Gly
385                 390                 395                 400
Leu Gly Val Ser Val Thr Gln Tyr Thr Lys Leu Ser His Gln Leu Ile
                405                 410                 415
Ser Asp Val Gln Val Leu Ser Gly Thr Ile Gln Asp Leu Gln Asp Gln
            420                 425                 430
Val Asp Ser Leu Ala Glu Val Val Leu Gln Asn Arg Arg Gly Leu Asp
        435                 440                 445
Leu Leu Thr Ala Glu Gln Gly Gly Ile Cys Leu Ala Leu Gln Glu Lys
450                 455                 460
Cys Cys Phe Tyr Ala Asn Lys Ser Gly Ile Val Arg Asn Lys Ile Arg
465                 470                 475                 480
Thr Leu Gln Glu Glu Leu Gln Lys Arg Arg Glu Ser Leu Ala Ser Asn
                485                 490                 495
Pro Leu Trp Thr Gly Leu Gln Gly Phe Leu Pro Tyr Leu Leu Pro Leu
            500                 505                 510
Leu Gly Pro Leu Leu Thr Leu Leu Leu Ile Leu Thr Ile Gly Pro Cys
        515                 520                 525
Val Phe
    530

<210> SEQ ID NO 6
<211> LENGTH: 33
<212> TYPE: PRT
<213> ORGANISM: Artificial sequence
<220> FEATURE:
<223> OTHER INFORMATION: Cytoplasmic domain of Murine Leukemia Virus-A
      envelope glycoprotein

<400> SEQUENCE: 6

Asn Arg Leu Val Gln Phe Val Lys Asp Arg Ile Ser Val Val Gln Ala
1               5                   10                  15
Leu Val Leu Thr Gln Gln Tyr His Gln Leu Lys Pro Leu Glu Tyr Glu
            20                  25                  30
Pro

<210> SEQ ID NO 7
<211> LENGTH: 39
<212> TYPE: PRT
<213> ORGANISM: Artificial sequence
<220> FEATURE:
<223> OTHER INFORMATION: Signal peptide of the Murine Leukemia Virus-A
      envelope glycoprotein

<400> SEQUENCE: 7

Met Ala Arg Ser Thr Leu Ser Lys Pro Leu Lys Asn Lys Val Asn Pro
1               5                   10                  15
Arg Gly Pro Leu Ile Pro Leu Ile Leu Leu Met Leu Arg Gly Val Ser
            20                  25                  30
Thr Ala Ser Pro Gly Ser Ser
            35

<210> SEQ ID NO 8
<211> LENGTH: 976
```

<212> TYPE: PRT
<213> ORGANISM: Homo sapiens

<400> SEQUENCE: 8

```
Met Arg Gly Ala Arg Gly Ala Trp Asp Phe Leu Cys Val Leu Leu Leu
1               5                   10                  15

Leu Leu Arg Val Gln Thr Gly Ser Ser Gln Pro Ser Val Ser Pro Gly
            20                  25                  30

Glu Pro Ser Pro Ser Ile His Pro Gly Lys Ser Asp Leu Ile Val
        35                  40                  45

Arg Val Gly Asp Glu Ile Arg Leu Leu Cys Thr Asp Pro Gly Phe Val
    50                  55                  60

Lys Trp Thr Phe Glu Ile Leu Asp Glu Thr Asn Glu Asn Lys Gln Asn
65                  70                  75                  80

Glu Trp Ile Thr Glu Lys Ala Glu Ala Thr Asn Thr Gly Lys Tyr Thr
                85                  90                  95

Cys Thr Asn Lys His Gly Leu Ser Asn Ser Ile Tyr Val Phe Val Arg
            100                 105                 110

Asp Pro Ala Lys Leu Phe Leu Val Asp Arg Ser Leu Tyr Gly Lys Glu
        115                 120                 125

Asp Asn Asp Thr Leu Val Arg Cys Pro Leu Thr Asp Pro Glu Val Thr
130                 135                 140

Asn Tyr Ser Leu Lys Gly Cys Gln Gly Lys Pro Leu Pro Lys Asp Leu
145                 150                 155                 160

Arg Phe Ile Pro Asp Pro Lys Ala Gly Ile Met Ile Lys Ser Val Lys
                165                 170                 175

Arg Ala Tyr His Arg Leu Cys Leu His Cys Ser Val Asp Gln Glu Gly
            180                 185                 190

Lys Ser Val Leu Ser Glu Lys Phe Ile Leu Lys Val Arg Pro Ala Phe
        195                 200                 205

Lys Ala Val Pro Val Val Ser Val Ser Lys Ala Ser Tyr Leu Leu Arg
210                 215                 220

Glu Gly Glu Glu Phe Thr Val Thr Cys Thr Ile Lys Asp Val Ser Ser
225                 230                 235                 240

Ser Val Tyr Ser Thr Trp Lys Arg Glu Asn Ser Gln Thr Lys Leu Gln
                245                 250                 255

Glu Lys Tyr Asn Ser Trp His His Gly Asp Phe Asn Tyr Glu Arg Gln
            260                 265                 270

Ala Thr Leu Thr Ile Ser Ser Ala Arg Val Asn Asp Ser Gly Val Phe
        275                 280                 285

Met Cys Tyr Ala Asn Asn Thr Phe Gly Ser Ala Asn Val Thr Thr Thr
290                 295                 300

Leu Glu Val Val Asp Lys Gly Phe Ile Asn Ile Phe Pro Met Ile Asn
305                 310                 315                 320

Thr Thr Val Phe Val Asn Asp Gly Glu Asn Val Asp Leu Ile Val Glu
                325                 330                 335

Tyr Glu Ala Phe Pro Lys Pro Glu His Gln Gln Trp Ile Tyr Met Asn
            340                 345                 350

Arg Thr Phe Thr Asp Lys Trp Glu Asp Tyr Pro Lys Ser Glu Asn Glu
        355                 360                 365

Ser Asn Ile Arg Tyr Val Ser Glu Leu His Leu Thr Arg Leu Lys Gly
370                 375                 380

Thr Glu Gly Gly Thr Tyr Thr Phe Leu Val Ser Asn Ser Asp Val Asn
385                 390                 395                 400
```

```
Ala Ala Ile Ala Phe Asn Val Tyr Val Asn Thr Lys Pro Glu Ile Leu
                405                 410                 415
Thr Tyr Asp Arg Leu Val Asn Gly Met Leu Gln Cys Val Ala Ala Gly
            420                 425                 430
Phe Pro Glu Pro Thr Ile Asp Trp Tyr Phe Cys Pro Gly Thr Glu Gln
        435                 440                 445
Arg Cys Ser Ala Ser Val Leu Pro Val Asp Val Gln Thr Leu Asn Ser
    450                 455                 460
Ser Gly Pro Pro Phe Gly Lys Leu Val Val Gln Ser Ser Ile Asp Ser
465                 470                 475                 480
Ser Ala Phe Lys His Asn Gly Thr Val Glu Cys Lys Ala Tyr Asn Asp
            485                 490                 495
Val Gly Lys Thr Ser Ala Tyr Phe Asn Phe Ala Phe Lys Gly Asn Asn
        500                 505                 510
Lys Glu Gln Ile His Pro His Thr Leu Phe Thr Pro Leu Leu Ile Gly
    515                 520                 525
Phe Val Ile Val Ala Gly Met Met Cys Ile Ile Val Met Ile Leu Thr
530                 535                 540
Tyr Lys Tyr Leu Gln Lys Pro Met Tyr Glu Val Gln Trp Lys Val Val
545                 550                 555                 560
Glu Glu Ile Asn Gly Asn Asn Tyr Val Tyr Ile Asp Pro Thr Gln Leu
            565                 570                 575
Pro Tyr Asp His Lys Trp Glu Phe Pro Arg Asn Arg Leu Ser Phe Gly
        580                 585                 590
Lys Thr Leu Gly Ala Gly Ala Phe Gly Lys Val Val Glu Ala Thr Ala
    595                 600                 605
Tyr Gly Leu Ile Lys Ser Asp Ala Ala Met Thr Val Ala Val Lys Met
610                 615                 620
Leu Lys Pro Ser Ala His Leu Thr Glu Arg Glu Ala Leu Met Ser Glu
625                 630                 635                 640
Leu Lys Val Leu Ser Tyr Leu Gly Asn His Met Asn Ile Val Asn Leu
            645                 650                 655
Leu Gly Ala Cys Thr Ile Gly Gly Pro Thr Leu Val Ile Thr Glu Tyr
        660                 665                 670
Cys Cys Tyr Gly Asp Leu Leu Asn Phe Leu Arg Arg Lys Arg Asp Ser
    675                 680                 685
Phe Ile Cys Ser Lys Gln Glu Asp His Ala Glu Ala Leu Tyr Lys
690                 695                 700
Asn Leu Leu His Ser Lys Glu Ser Ser Cys Ser Asp Ser Thr Asn Glu
705                 710                 715                 720
Tyr Met Asp Met Lys Pro Gly Val Ser Tyr Val Val Pro Thr Lys Ala
            725                 730                 735
Asp Lys Arg Arg Ser Val Arg Ile Gly Ser Tyr Ile Glu Arg Asp Val
        740                 745                 750
Thr Pro Ala Ile Met Glu Asp Asp Glu Leu Ala Leu Asp Leu Glu Asp
    755                 760                 765
Leu Leu Ser Phe Ser Tyr Gln Val Ala Lys Gly Met Ala Phe Leu Ala
770                 775                 780
Ser Lys Asn Cys Ile His Arg Asp Leu Ala Ala Arg Asn Ile Leu Leu
785                 790                 795                 800
Thr His Gly Arg Ile Thr Lys Ile Cys Asp Phe Gly Leu Ala Arg Asp
            805                 810                 815
```

```
Ile Lys Asn Asp Ser Asn Tyr Val Val Lys Gly Asn Ala Arg Leu Pro
            820                 825                 830

Val Lys Trp Met Ala Pro Glu Ser Ile Phe Asn Cys Val Tyr Thr Phe
            835                 840                 845

Glu Ser Asp Val Trp Ser Tyr Gly Ile Phe Leu Trp Glu Leu Phe Ser
850                 855                 860

Leu Gly Ser Ser Pro Tyr Pro Gly Met Pro Val Asp Ser Lys Phe Tyr
865                 870                 875                 880

Lys Met Ile Lys Glu Gly Phe Arg Met Leu Ser Pro Glu His Ala Pro
            885                 890                 895

Ala Glu Met Tyr Asp Ile Met Lys Thr Cys Trp Asp Ala Asp Pro Leu
            900                 905                 910

Lys Arg Pro Thr Phe Lys Gln Ile Val Gln Leu Ile Glu Lys Gln Ile
            915                 920                 925

Ser Glu Ser Thr Asn His Ile Tyr Ser Asn Leu Ala Asn Cys Ser Pro
            930                 935                 940

Asn Arg Gln Lys Pro Val Val Asp His Ser Val Arg Ile Asn Ser Val
945                 950                 955                 960

Gly Ser Thr Ala Ser Ser Ser Gln Pro Leu Leu Val His Asp Asp Val
            965                 970                 975

<210> SEQ ID NO 9
<211> LENGTH: 189
<212> TYPE: PRT
<213> ORGANISM: Artificial sequence
<220> FEATURE:
<223> OTHER INFORMATION: Extracellular domain of the human SCF cytokine

<400> SEQUENCE: 9

Glu Gly Ile Cys Arg Asn Arg Val Thr Asn Asn Val Lys Asp Val Thr
1               5                   10                  15

Lys Leu Val Ala Asn Leu Pro Lys Asp Tyr Met Ile Thr Leu Lys Tyr
            20                  25                  30

Val Pro Gly Met Asp Val Leu Pro Ser His Cys Trp Ile Ser Glu Met
            35                  40                  45

Val Val Gln Leu Ser Asp Ser Leu Thr Asp Leu Leu Asp Lys Phe Ser
    50                  55                  60

Asn Ile Ser Glu Gly Leu Ser Asn Tyr Ser Ile Ile Asp Lys Leu Val
65                  70                  75                  80

Asn Ile Val Asp Asp Leu Val Glu Cys Val Lys Glu Asn Ser Ser Lys
                85                  90                  95

Asp Leu Lys Lys Ser Phe Lys Ser Pro Glu Pro Arg Leu Phe Thr Pro
            100                 105                 110

Glu Glu Phe Phe Arg Ile Phe Asn Arg Ser Ile Asp Ala Phe Lys Asp
            115                 120                 125

Phe Val Val Ala Ser Glu Thr Ser Asp Cys Val Val Ser Ser Thr Leu
    130                 135                 140

Ser Pro Glu Lys Asp Ser Arg Val Ser Val Thr Lys Pro Phe Met Leu
145                 150                 155                 160

Pro Pro Val Ala Ala Ser Ser Leu Arg Asn Asp Ser Ser Ser Ser Asn
                165                 170                 175

Arg Lys Ala Lys Asn Pro Pro Gly Asp Ser Ser Leu His
            180                 185

<210> SEQ ID NO 10
<211> LENGTH: 558
```

```
<212> TYPE: PRT
<213> ORGANISM: Artificial sequence
<220> FEATURE:
<223> OTHER INFORMATION: N-terminal domain of the Fowl Plague Virus
      hemagglutinin

<400> SEQUENCE: 10
```

| | | | | | | | | | | | | | | |
|---|---|---|---|---|---|---|---|---|---|---|---|---|---|---|
| Ile | Glu | Gly | Arg | Gln | Asp | Leu | Pro | Gly | Asn | Asp | Asn | Ser | Asp | Lys | Ile |
| 1 | | | | 5 | | | | | 10 | | | | | 15 | |
| Cys | Leu | Gly | His | His | Ala | Val | Ser | Asn | Gly | Thr | Lys | Val | Asn | Thr | Leu |
| | | | 20 | | | | | 25 | | | | | 30 | | |
| Thr | Glu | Arg | Gly | Val | Glu | Val | Val | Asn | Ala | Thr | Glu | Thr | Val | Glu | Arg |
| | | 35 | | | | | 40 | | | | | 45 | | | |
| Thr | Asn | Ile | Pro | Lys | Ile | Cys | Ser | Lys | Gly | Lys | Arg | Thr | Thr | Asp | Leu |
| 50 | | | | | 55 | | | | | 60 | | | | | |
| Gly | Gln | Cys | Gly | Leu | Leu | Gly | Thr | Ile | Thr | Gly | Pro | Pro | Gln | Cys | Asp |
| 65 | | | | | 70 | | | | | 75 | | | | | 80 |
| Gln | Phe | Leu | Glu | Phe | Ser | Ala | Asp | Leu | Ile | Ile | Glu | Arg | Arg | Glu | Gly |
| | | | | 85 | | | | | 90 | | | | | 95 | |
| Asn | Asp | Val | Cys | Tyr | Pro | Gly | Lys | Phe | Val | Asn | Glu | Glu | Ala | Leu | Arg |
| | | | 100 | | | | | 105 | | | | | 110 | | |
| Gln | Ile | Leu | Arg | Gly | Ser | Gly | Ile | Asp | Lys | Glu | Thr | Met | Gly | Phe |
| | | 115 | | | | | 120 | | | | | 125 | | | |
| Thr | Tyr | Ser | Gly | Ile | Arg | Thr | Asn | Gly | Thr | Thr | Ser | Ala | Cys | Arg | Arg |
| | | 130 | | | | | 135 | | | | | 140 | | | |
| Ser | Gly | Ser | Ser | Phe | Tyr | Ala | Glu | Met | Glu | Trp | Leu | Leu | Ser | Asn | Thr |
| 145 | | | | | 150 | | | | | 155 | | | | | 160 |
| Asp | Asn | Ala | Ser | Phe | Pro | Gln | Met | Thr | Lys | Ser | Tyr | Lys | Asn | Thr | Arg |
| | | | | 165 | | | | | 170 | | | | | 175 | |
| Arg | Glu | Ser | Ala | Leu | Ile | Val | Trp | Gly | Ile | His | His | Ser | Gly | Ser | Thr |
| | | | 180 | | | | | 185 | | | | | 190 | | |
| Thr | Glu | Gln | Thr | Lys | Leu | Tyr | Gly | Ser | Gly | Asn | Lys | Leu | Ile | Thr | Val |
| | | 195 | | | | | 200 | | | | | 205 | | | |
| Gly | Ser | Ser | Lys | Tyr | His | Gln | Ser | Phe | Val | Pro | Ser | Pro | Gly | Thr | Arg |
| 210 | | | | | 215 | | | | | 220 | | | | | |
| Pro | Gln | Ile | Asn | Gly | Gln | Ser | Gly | Arg | Ile | Asp | Phe | His | Trp | Leu | Ile |
| 225 | | | | | 230 | | | | | 235 | | | | | 240 |
| Leu | Asp | Pro | Asn | Asp | Thr | Val | Thr | Phe | Ser | Phe | Asn | Gly | Ala | Phe | Ile |
| | | | | 245 | | | | | 250 | | | | | 255 | |
| Ala | Pro | Asn | Arg | Ala | Ser | Phe | Leu | Arg | Gly | Lys | Ser | Met | Gly | Ile | Gln |
| | | | 260 | | | | | 265 | | | | | 270 | | |
| Ser | Asp | Val | Gln | Val | Asp | Ala | Asn | Cys | Glu | Gly | Glu | Cys | Tyr | His | Ser |
| | | 275 | | | | | 280 | | | | | 285 | | | |
| Gly | Gly | Thr | Ile | Thr | Ser | Arg | Leu | Pro | Phe | Gln | Asn | Ile | Asn | Ser | Arg |
| | | 290 | | | | | 295 | | | | | 300 | | | |
| Ala | Val | Gly | Lys | Cys | Pro | Arg | Tyr | Val | Lys | Gln | Glu | Ser | Leu | Leu | Leu |
| 305 | | | | | 310 | | | | | 315 | | | | | 320 |
| Ala | Thr | Gly | Met | Lys | Asn | Val | Pro | Glu | Pro | Ser | Lys | Lys | Arg | Lys | Lys |
| | | | | 325 | | | | | 330 | | | | | 335 | |
| Arg | Gly | Leu | Phe | Gly | Ala | Ile | Ala | Gly | Phe | Ile | Glu | Asn | Gly | Trp | Glu |
| | | | 340 | | | | | 345 | | | | | 350 | | |
| Gly | Leu | Val | Asp | Gly | Trp | Tyr | Gly | Phe | Arg | His | Gln | Asn | Ala | Gln | Gly |
| | | | 355 | | | | | 360 | | | | | 365 | | |
| Glu | Gly | Thr | Ala | Ala | Asp | Tyr | Lys | Ser | Thr | Gln | Ser | Ala | Ile | Asp | Gln |
| | | 370 | | | | | 375 | | | | | 380 | | | |

```
Ile Thr Gly Lys Leu Asn Arg Leu Ile Glu Lys Thr Asn Gln Gln Phe
385                 390                 395                 400

Glu Leu Ile Asp Asn Glu Phe Thr Glu Val Glu Lys Gln Ile Gly Asn
            405                 410                 415

Leu Ile Asn Trp Thr Lys Asp Ser Ile Thr Glu Val Trp Ser Tyr Asn
            420                 425                 430

Ala Glu Leu Ile Val Ala Met Glu Asn Gln His Thr Ile Asp Leu Ala
            435                 440                 445

Asp Ser Glu Met Asn Arg Leu Tyr Glu Arg Val Arg Lys Gln Leu Arg
450                 455                 460

Glu Asn Ala Glu Glu Asp Gly Thr Gly Cys Phe Glu Ile Phe His Lys
465                 470                 475                 480

Cys Asp Asp Asp Cys Met Ala Ser Ile Arg Asn Asn Thr Tyr Asp His
                485                 490                 495

Ser Lys Tyr Arg Glu Glu Ala Met Gln Asn Arg Ile Gln Ile Asp Pro
            500                 505                 510

Val Lys Leu Ser Ser Gly Tyr Lys Asp Val Ile Leu Trp Phe Ser Phe
            515                 520                 525

Gly Ala Ser Cys Phe Leu Leu Leu Ala Ile Ala Met Gly Leu Val Phe
530                 535                 540

Ile Cys Val Lys Asn Gly Asn Met Arg Cys Thr Ile Cys Ile
545                 550                 555

<210> SEQ ID NO 11
<211> LENGTH: 6907
<212> TYPE: DNA
<213> ORGANISM: Artificial sequence
<220> FEATURE:
<223> OTHER INFORMATION: Plasmid encoding the fusion protein of SEQ ID
      NO: 2

<400> SEQUENCE: 11
gcggccgctc tagagagctt ggcccattgc atacgttgta tccatatcat aatatgtaca      60
tttatattgg ctcatgtcca acattaccgc catgttgaca ttgattattg actagttatt     120
aatagtaatc aattacgggg tcattagttc atagcccata tatggagttc cgcgttacat     180
aacttacggt aaatggcccg cctggctgac cgcccaacga cccccgccca ttgacgtcaa     240
taatgacgta tgttcccata gtaacgccaa tagggacttt ccattgacgt caatgggtgg     300
agtatttacg gtaaactgcc cacttggcag tacatcaagt gtatcatatg ccaagtacgc     360
cccctattga cgtcaatgac ggtaaatggc ccgcctggca ttatgcccag tacatgacct     420
tatgggactt tcctacttgg cagtacatct acgtattagt catcgctatt accatggtga     480
tgcggttttg gcagtacatc aatgggcgtg gatagcggtt tgactcacgg ggatttccaa     540
gtctccaccc cattgacgtc aatgggagtt tgttttggca ccaaaatcaa cgggactttc     600
caaaatgtcg taacaactcc gccccattga cgcaaatggg cggtaggcgt gtacggtggg     660
aggtctatat aagcagagct cgtttagtga accgtcagat cgcctggaga cgccatccac     720
gctgttttga cctccataga agacaccggg accgatccag cctccggtcg accgatcctg     780
agaacttcag ggtgagtttg ggacccttga ttgttctttc ttttttcgct attgtaaaat     840
tcatgttata tggagggggc aaagttttca gggtgttgtt tagaatggga agatgtccct     900
tgtatcacca tggaccctca tgataatttt gtttctttca ctttctactc tgttgacaac     960
cattgtctcc tcttattttc ttttcatttt ctgtaacttt tcgttaaac tttagcttgc    1020
```

```
atttgtaacg aatttttaaa ttcacttttg tttatttgtc agattgtaag tactttctct      1080
aatcactttt ttttcaaggc aatcagggta tattatattg tacttcagca cagttttaga      1140
gaacaattgt tataattaaa tgataaggta gaatatttct gcatataaat tctggctggc      1200
gtggaaatat tcttattggt agaaacaact acaccctggt catcatcctg cctttctctt      1260
tatggttaca atgatataca ctgtttgaga tgaggataaa atactctgag tccaaaccgg      1320 gccctctgc taaccatgtt catgccttct tctctttcct acagctcctg ggcaacgtgc       1380
tggttgttgt gctgtctcat cattttggca aagaattcct cgacggatcc ctcgattaag      1440
ataagactct cccgtgtctg actgctaatc caccttgtcc ctgtactaac ccaaaatgaa      1500
actcccaaca ggaatggtca ttttatgtag cctaataata gttcgggcag ggtttgacga      1560
cccccgcaag gctatcgcat tagtacaaaa acaacatggt aaaccatgcg aatgcagcgg      1620
agggcaggta tccgaggccc caccgaactc catccaacag gtaacttgcc caggcaagac      1680
ggcctactta atgaccaacc aaaaatggaa atgcagagtc actccaaaaa tctcacctag      1740
cgggggagaa ctccagaact gccctgtaa cactttccag gactcgatgc acagttcttg       1800
ttatactgaa taccggcaat gcaggcgaat aataagaca tactacacgg ccaccttgct       1860
taaaatacgg tctgggagcc tcaacgaggt acagatatta caaaacccca atcagctcct      1920
acagtcccct tgtaggggct ctataaatca gcccgtttgc tggagtgcca cagcccccat      1980
ccatatctcc gatggtggag gaccctcga tactaagaga gtgtggacag tccaaaaaag       2040
gctagaacaa attcataagg ctatgactcc tgaacttcaa taccacccct tagccctgcc      2100
caaagtcaga gatgacctta gccttgatgc acggactttt gatatcctga ataccacttt      2160
taggttactc cagatgtcca attttagcct tgcccaagat tgttggctct gtttaaaact      2220
aggtacccct acccctcttg cgatacccac tccctcttta acctactccc tagcagactc      2280
cctagcgaat gcctcctgtc agattatacc tcccctcttg gttcaaccga tgcagttctc      2340
caactcgtcc tgtttatctt cccctttcat taacgatacg gaacaaatag acttaggtgc      2400
agtcaccttt actaactgca cctctgtagc caatgtcagt agtcctttat gtgccctaaa      2460
cgggtcagtc ttcctctgtg gaaataacat ggcatacacc tatttacccc aaaactggac      2520
cagactttgc gtccaagcct ccctcctccc cgacattgac atcaacccgg gggatgagcc      2580
agtccccatt cctgccattg atcattatat acatagacct aaacgagctg tacagttcat      2640 cccctttacta gctggactgg gaatcaccgc agcattcacc accggagcta caggcctagg      2700
tgtctccgtc acccagtata caaaattatc ccatcagtta atatctgatg tccaagtctt      2760
atccggtacc atacaagatt tacaagacca ggtagactcg ttagctgaag tagttctcca      2820
aaataggagg ggactggacc tactaacggc agaacaagga ggaatttgtt tagccttaca      2880
agaaaaatgc tgttttatg ctaacaagtc aggaattgtg agaaacaaaa taagaaccct       2940
acaagaagaa ttacaaaaac gcagggaaag cctggcatcc aaccctctct ggaccgggct      3000
gcagggcttt cttccgtacc tcctacctct cctgggaccc ctactcaccc tcctactcat      3060
actaaccatt gggccatgcg ttttcaatcg attagttcaa tttgttaaag acaggatctc      3120
agtagtccag gctttagtcc tgactcaaca ataccaccag ctaaaaccac tagaatacga      3180
gccgtgacca tggtgctggc ccagcaatac caagcactca aagctgagga agaagctcag      3240
gattgagctt ccgggacaaa agcaggggg aatgagaagt cagaacccccc cacctttgct     3300 acataaaataa ccgctttcat ttcgcttctg taaaaccgct tatgcgcccc accctaaccg      3360
ctttcatttc gcttctgtaa aaccgcttat gcgccccacc ctagccggaa agtccccagc      3420
```

```
cgctacgcaa cccgggcccc gagttgcatc agccgttcgc aacccgggct ccgagttgca    3480
tcagccgaaa gaaacttcat ttcccaagct tcgaggatc cgtcgaggaa ttcactcctc     3540
aggtgcaggc tgcctatcag aaggtggtgg ctggtgtggc caatgccctg gctcacaaat    3600
accactgaga tcttttttccc tctgccaaaa attatgggga catcatgaag cccttgagc    3660
atctgacttc tggctaataa aggaaattta ttttcattgc aatagtgtgt tggaattttt    3720
tgtgtctctc actcggaagg acatatggga gggcaaatca tttaaaacat cagaatgagt    3780
atttggttta gagtttggca acatatgccc atatgctggc tgccatgaac aaaggttggc    3840
tataaagagg tcatcagtat atgaaacagc cccctgctgt ccattcctta ttccatagaa    3900
aagccttgac ttgaggttag attttttta tattttgttt tgtgttattt ttttctttaa     3960
catccctaaa attttcctta catgttttac tagccagatt tttcctcctc tcctgactac    4020
tcccagtcat agctgtccct cttctcttat ggagatccct cgacggatcg ccgcaattc     4080
gtaatcatgt catagctgtt tcctgtgtga aattgttatc cgctcacaat tccacacaac    4140
atacgagccg aagcataaa gtgtaaagcc tggggtgcct aatgagtgag ctaactcaca     4200
ttaattgcgt tgcgctcact gcccgctttc cagtcgggaa acctgtcgtg ccagctgcat    4260
taatgaatcg gccaacgcgc ggggagaggc ggtttgcgta ttgggcgctc ttccgcttcc    4320
tcgctcactg actcgctgcg ctcggtcgtt cggctgcggc gagcggtatc agctcactca    4380
aaggcggtaa tacggttatc cacagaatca ggggataacg caggaaagaa catgtgagca    4440
aaaggccagc aaaaggccag gaaccgtaaa aaggccgcgt tgctggcgtt tttccatagg    4500
ctccgccccc ctgacgagca tcacaaaaat cgacgctcaa gtcagaggtg gcgaaacccg    4560
acaggactat aaagatacca ggcgtttccc cctggaagct ccctcgtgcg ctctcctgtt    4620
ccgaccctgc cgcttaccgg atacctgtcc gcctttctcc cttcgggaag cgtggcgctt    4680
tctcatagct cacgctgtag gtatctcagt tcggtgtagg tcgttcgctc caagctgggc    4740
tgtgtgcacg aaccccccgt tcagcccgac cgctgcgcct tatccggtaa ctatcgtctt    4800
gagtccaacc cggtaagaca cgacttatcg ccactggcag cagccactgg taacaggatt    4860
agcagagcga ggtatgtagg cggtgctaca gagttcttga agtggtggcc taactacggc    4920
tacactagaa gaacagtatt tggtatctgc gctctgctga agccagttac cttcggaaaa    4980
agagttggta gctcttgatc cggcaaacaa accaccgctg gtagcggtgg tttttttgtt    5040
tgcaagcagc agattacgcg cagaaaaaaa ggatctcaag aagatccttt gatcttttct    5100
acggggtctg acgctcagtg gaacgaaaac tcacgttaag ggattttggt catgagatta    5160
tcaaaaagga tcttcaccta gatccttta aattaaaaat gaagttttaa atcaatctaa     5220
agtatatatg agtaaacttg gtctgacagt taccaatgct taatcagtga ggcacctatc    5280
tcagcgatct gtctatttcg ttcatccata gttgcctgac tccccgtcgt gtagataact    5340
acgatacggg agggcttacc atctggcccc agtgctgcaa tgataccgcg agacccacgc    5400
tcaccggctc cagatttatc agcaataaac cagccagccg aagggccga gcgcagaagt     5460
ggtcctgcaa ctttatccgc ctccatccag tctattaatt gttgccggga agctagagta    5520
agtagttcgc cagttaatag tttgcgcaac gttgttgcca ttgctacagg catcgtggtg    5580
tcacgctcgt cgtttggtat ggcttcattc agctccggtt cccaacgatc aaggcgagtt    5640
acatgatccc ccatgttgtg caaaaaagcg gttagctcc ttcggtcctc cgatcgttgt     5700
cagaagtaag ttggccgcag tgttatcact catggttatg gcagcactgc ataattctct    5760
```

```
tactgtcatg ccatccgtaa gatgcttttc tgtgactggt gagtactcaa ccaagtcatt    5820
ctgagaatag tgtatgcggc gaccgagttg ctcttgcccg gcgtcaatac gggataatac    5880
cgcgccacat agcagaactt taaaagtgct catcattgga aaacgttctt cggggcgaaa    5940
actctcaagg atcttaccgc tgttgagatc cagttcgatg taacccactc gtgcacccaa    6000
ctgatcttca gcatctttta ctttcaccag cgtttctggg tgagcaaaaa caggaaggca    6060
aaatgccgca aaaagggaa taagggcgac acggaaatgt tgaatactca tactcttcct    6120
ttttcaatat tattgaagca tttatcaggg ttattgtctc atgagcggat acatatttga    6180
atgtatttag aaaaataaac aaataggggt tccgcgcaca tttccccgaa aagtgccacc    6240
taaattgtaa gcgttaatat tttgttaaaa ttcgcgttaa attttgtta aatcagctca    6300 ttttttaacc aataggccga atcggcaaa atcccttata atcaaaaga atagaccgag    6360 ataggttga gtgttgttcc agtttggaac aagagtccac tattaaagaa cgtggactcc    6420
aacgtcaaag ggcgaaaaac cgtctatcag ggcgatggcc cactacgtga accatcaccc    6480
taatcaagtt ttttggggtc gaggtgccgt aaagcactaa atcggaaccc taaagggagc    6540
ccccgattta gagcttgacg gggaaagccg gcgaacgtgg cgagaaagga agggaagaaa    6600
gcgaaaggag cgggcgctag gcgctggca agtgtagcgg tcacgctgcg cgtaaccacc    6660
acacccgccg cgcttaatgc gccgctacag ggcgcgtccc attcgccatt caggctgcgc    6720
aactgttggg aagggcgatc ggtgcgggcc tcttcgctat tacgccagct ggcgaaaggg    6780
ggatgtgctg caaggcgatt aagttgggta acgccagggt ttccccagtc acgacgttgt    6840
aaaacgacgg ccagtgagcg cgcgtaatac gactcactat agggcgaatt ggagctccac    6900
cgcggtg                                                              6907
```

<210> SEQ ID NO 12
<211> LENGTH: 7269
<212> TYPE: DNA
<213> ORGANISM: Artificial sequence
<220> FEATURE:
<223> OTHER INFORMATION: Plasmid encoding the fusion protein of SEQ ID
    NO: 4

<400> SEQUENCE: 12

```
gatcttttc cctctgccaa aaattatggg gacatcatga agcccttga gcatctgact      60 tctggctaat aaaggaaatt tattttcatt gcaatagtgt gttggaattt tttgtgtctc    120
tcactcggaa ggacatatgg gagggcaaat catttaaaac atcagaatga gtatttggtt    180
tagagtttgg caacatatgc ccatatgctg gctgccatga acaaaggttg gctataaaga    240
ggtcatcagt atatgaaaca gccccctgct gtccattcct tattccatag aaaagccttg    300
acttgaggtt agattttttt tatatttgt tttgtgttat tttttctttt aacatcccta    360
aaattttcct tacatgtttt actagccaga ttttcctcc tctcctgact actcccagtc    420
atagctgtcc ctcttctctt atggagatcc ctcgacggat cggccgcaat tcgtaatcat    480
gtcatagctg tttcctgtgt gaaattgtta tccgctcaca attccacaca atacgagc     540 cggaagcata aagtgtaaag cctggggtgc ctaatgagtg agctaactca cattaattgc    600
gttgcgctca ctgcccgctt ccagtcggg aaacctgtcg tgccagctgc attaatgaat    660
cggccaacgc gcgggagag gcggtttgcg tattgggcgc tcttccgctt cctcgctcac    720
tgactcgctg cgctcggtcg ttcggctgcg gcgagcggta tcagctcact caaaggcggt    780
aatacggtta ccacagaat caggggataa cgcaggaaag aacatgtgag caaaaggcca    840
```

-continued

```
gcaaaaggcc aggaaccgta aaaaggccgc gttgctggcg ttttttccata ggctccgccc    900
ccctgacgag catcacaaaa atcgacgctc aagtcagagg tggcgaaacc cgacaggact    960
ataaagatac caggcgtttc ccctggaag ctccctcgtg cgctctcctg ttccgaccct   1020
gccgcttacc ggatacctgt ccgcctttct cccttcggga agcgtggcgc tttctcatag   1080
ctcacgctgt aggtatctca gttcggtgta ggtcgttcgc tccaagctgg gctgtgtgca   1140
cgaacccccc gttcagcccg accgctgcgc cttatccggt aactatcgtc ttgagtccaa   1200
cccggtaaga cacgacttat cgccactggc agcagccact ggtaacagga ttagcagagc   1260
gaggtatgta ggcggtgcta cagagttctt gaagtggtgg cctaactacg gctacactag   1320
aagaacagta tttggtatct gcgctctgct gaagccagtt accttcggaa aaagagttgg   1380
tagctcttga tccggcaaac aaaccaccgc tggtagcggt ggtttttttg tttgcaagca   1440
gcagattacg cgcagaaaaa aaggatctca agaagatcct ttgatctttt ctacggggtc   1500
tgacgctcag tggaacgaaa actcacgtta agggattttg gtcatgagat tatcaaaaag   1560
gatcttcacc tagatccttt taaattaaaa atgaagtttt aaatcaatct aaagtatata   1620
tgagtaaact tggtctgaca gttaccaatg cttaatcagt gaggcaccta tctcagcgat   1680
ctgtctattt cgttcatcca tagttgcctg actccccgtc gtgtagataa ctacgatacg   1740
ggagggctta ccatctggcc ccagtgctgc aatgataccg cgagacccac gctcaccggc   1800
tccagattta tcagcaataa accagccagc cggaagggcc gagcgcagaa gtggtcctgc   1860
aactttatcc gcctccatcc agtctattaa ttgttgccgg gaagctagag taagtagttc   1920
gccagttaat agtttgcgca acgttgttgc cattgctaca ggcatcgtgg tgtcacgctc   1980
gtcgtttggt atggcttcat tcagctccgg ttcccaacga tcaaggcgag ttacatgatc   2040
ccccatgttg tgcaaaaaag cggttagct ccttcggtcc tccgatcgtt gtcagaagta   2100
agttggccgc agtgttatca ctcatggtta tggcagcact gcataattct cttactgtca   2160
tgccatccgt aagatgcttt tctgtgactg gtgagtactc aaccaagtca ttctgagaat   2220
agtgtatgcg gcgaccgagt tgctcttgcc cggcgtcaat acgggataat accgcgccac   2280
atagcagaac tttaaaagtg ctcatcattg gaaaacgttc ttcggggcga aaactctcaa   2340
ggatcttacc gctgttgaga tccagttcga tgtaacccac tcgtgcaccc aactgatctt   2400
cagcatcttt tactttcacc agcgtttctg ggtgagcaaa aacaggaagg caaaatgccg   2460
caaaaaggg aataagggcg acacggaaat gttgaatact catactcttc ctttttcaat   2520
attattgaag catttatcag ggttattgtc tcatgagcgg atacatattt gaatgtattt   2580
agaaaaataa acaaataggg gttccgcgca catttccccg aaaagtgcca cctaaattgt   2640
aagcgttaat attttgttaa aattcgcgtt aaattttgt taaatcagct catttttaa   2700
ccaataggcc gaaatcggca aaatccctta taaatcaaaa gaatagaccg agatagggtt   2760
gagtgttgtt ccagtttgga acaagagtcc actattaaag aacgtggact ccaacgtcaa   2820
agggcgaaaa accgtctatc agggcgatgg cccactacgt gaaccatcac cctaatcaag   2880
ttttttgggg tcgaggtgcc gtaaagcact aaatcggaac cctaaaggga gcccccgatt   2940
tagagcttga cggggaaagc cggcgaacgt ggcgagaaag gaaggaaga aagcgaaagg   3000
agcgggcgct agggcgctgg caagtgtagc ggtcacgctg cgcgtaacca ccacacccgc   3060
cgcgcttaat gcgccgctac agggcgcgtc ccattcgcca ttcaggctgc gcaactgttg   3120
ggaagggcga tcggtgcggg cctcttcgct attacgccag ctggcgaaag ggggatgtgc   3180
tgcaaggcga ttaagttggg taacgccagg gttttcccag tcacgacgtt gtaaaacgac   3240
```

```
ggccagtgag cgcgcgtaat acgactcact atagggcgaa ttggagctcc accgcggtgg   3300
cggccggccg cgctctagag agcttggccc attgcatacg ttgtatccat atcataatat   3360
gtacatttat attggctcat gtccaacatt accgccatgt tgacattgat tattgactag   3420
ttattaatag taatcaatta cggggtcatt agttcatagc ccatatatgg agttccgcgt   3480
tacataactt acggtaaatg gcccgcctgg ctgaccgccc aacgaccccc gcccattgac   3540
gtcaataatg acgtatgttc ccatagtaac gccaataggg actttccatt gacgtcaatg   3600
ggtggagtat ttacggtaaa ctgcccactt ggcagtacat caagtgtatc atatgccaag   3660 tacgcccccct attgacgtca atgacggtaa atggcccgcc tggcattatg cccagtacat   3720
gaccttatgg gactttccta cttggcagta catctacgta ttagtcatcg ctattaccat   3780
ggtgatgcgg ttttggcagt acatcaatgg gcgtggatag cggtttgact cacggggatt   3840
tccaagtctc cacccccattg acgtcaatgg gagtttgttt tggcaccaaa atcaacggga   3900
ctttccaaaa tgtcgtaaca actccgcccc attgacgcaa atgggcggta ggcgtgtacg   3960
gtgggaggtc tatataagca gagctcgttt agtgaaccgt cagatcgcct ggagacgcca   4020
tccacgctgt tttgacctcc atagaagaca ccgggaccga tccagcctcc ggtcgaccga   4080
tcctgagaac ttcagggtga gtttggggac ccttgattgt tctttctttt tcgctattgt   4140
aaaattcatg ttatatggag gggcaaagt tttcagggtg ttgtttagaa tgggaagatg   4200
tcccttgtat caccatggac cctcatgata attttgtttc tttcactttc tactctgttg   4260
acaaccattg tctcctctta ttttcttttc attttctgta acttttttcgt taaactttag   4320 cttgcatttg taacgaattt ttaaattcac ttttgtttat ttgtcagatt gtaagtactt   4380
tctctaatca ttttttttc aaggcaatca gggtatatta tattgtactt cagcacagtt   4440
ttagagaaca attgttataa ttaaatgata aggtagaata tttctgcata taaattctgg   4500
ctggcgtgga aatattctta ttggtagaaa caactacacc ctggtcatca tcctgccttt   4560
ctctttatgg ttacaatgat atacactgtt tgagatgagg ataaaatact ctgagtccaa   4620
accgggcccc tctgctaacc atgttcatgc cttcttctct ttcctacagc tcctgggcaa   4680
cgtgctggtt gttgtgctgt ctcatcattt tggcaaagaa ttctagactg acatggcgcg   4740
ttcaacgctc tcaaaacccc ttaaaaataa ggttaacccg cgaggccccc taatccccctt   4800 aattcttctg atgctcagag gggtcagtac tgcttcgccc ggctccagtg cggcccagcc   4860
ggccgaaggg atctgcagga atcgtgtgac taataatgta aaagacgtca ctaaattggt   4920
ggcaaatctt ccaaaagact acatgataac cctcaaatat gtccccggga tggatgtttt   4980
gccaagtcat tgttggataa gcgagatggt agtacaattg tcagacagct tgactgatct   5040
tctggacaag ttttcaaata tttctgaagg cttgagtaat tattccatca tagacaaact   5100
tgtgaatata gtcgatgacc ttgtggagtg cgtcaaagaa aactcatcta aggatctaaa   5160
aaaatcattc aagagcccag aacccaggct ctttactcct gaagaattct ttagaatttt   5220
taatagatcc attgatgcct tcaaggactt tgtagtggca tctgaaacta gtgattgtgt   5280
ggtttcttca acattaagtc ctgagaaaga ttccagagtc agtgtcacaa aaccatttat   5340
gttaccccct gttgcagcca gctcccttag gaatgacagc agtagcagta ataggaaggc   5400
caaaaatccc cctggagact ccagcctaca cgcggccgca atcgagggaa ggcaagacct   5460
tccaggaaat gacaacagcg acaaaatttg tcttggacat catgctgtat caaatggcac   5520
caaagtaaac acactcactg agagaggagt agaagttgtc aatgcaacgg aaacagtgga   5580
```

-continued

```
gcggacaaac atccccaaaa tttgctcaaa agggaaaaga accactgatc ttggccaatg    5640
cggactgtta gggaccatta ccggaccacc tcaatgcgac caatttctag aattttcagc    5700
tgatctaata atcgagagac gagaaggaaa tgatgtttgt acccggggga agtttgttaa    5760
tgaagaggca ttgcgacaaa tcctcagagg atcaggtggg attgacaaag aaacaatggg    5820
attcacatat agtggaataa ggaccaacgg aacaactagt gcatgtagaa gatcagggtc    5880
ttcattctat gcagaaatgg agtggctcct gtcaaataca gacaatgctt ctttcccaca    5940
aatgacaaaa tcatacaaaa acacaaggag agaatcagct ctgatagtat ggggaatcca    6000
ccattcagga tcaaccaccg aacagaccaa actatatggg agtggaaata aactgataac    6060
agtcgggagt tccaaatatc atcaatcttt tgtgccgagt ccaggaacac gaccgcagat    6120
aaatggccag tccggacgga ttgattttca ttggttgatc ttggatccca atgatacagt    6180 tactttagt ttcaatgggg ctttcatagc tccaaatcgt gccagcttct tgaggggaaa    6240
gtccatgggg atccagagcg atgtgcaggt tgatgccaat tgcgaagggg aatgctacca    6300
cagtggaggg actataacaa gcagattgcc ttttcaaaac atcaatagca gagcagttgg    6360
caaatgccca agatatgtaa aacaggaaag tttattattg caactgggga tgaagaacgt    6420
tcccgaacct tccaaaaaaa ggaaaaaaag aggcctgttt ggcgctatag cagggtttat    6480
tgaaaatggt tgggaaggtc tggtcgacgg gtggtacggt ttcaggcatc agaatgcaca    6540
aggagaagga actgcagcag actacaaaag cacccaatcg gcaattgatc agataaccgg    6600
aaagttaaat agactcattg agaaaccaa ccagcaattt gagctaatag ataatgaatt    6660
cactgaggtg gaaaagcaga ttggcaattt aattaactgg accaaagact ccatcacaga    6720
agtatggtct acaatgctg aacttattgt ggcaatggaa aaccagcaca ctattgattt    6780
ggctgattca gagatgaaca ggctgtatga gcgagtgagg aaacaattaa gggaaaatgc    6840
tgaagaggat ggtactggtt gctttgaaat ttttcataaa tgtgacgatg attgtatggc    6900
tagtataagg aacaatactt atgatcacag caaatacaga gaagaagcga tgcaaaatag    6960
aatacaaatt gacccagtca aattgagtag tggctacaaa gatgtgatac tttggtttag    7020
cttcggggca tcatgctttt tgcttcttgc cattgcaatg ggccttgttt tcatatgtgt    7080
gaagaacgga aacatgcggt gcactatttg tatataagtt tggaaaaaaa caccttgtt    7140 tctactctct agaggatccc cgggcgcgaa cgtggaagat ccgtcgagga attcactcct    7200
caggtgcagg ctgcctatca gaaggtggtg gctggtgtgg ccaatgccct ggctcacaaa    7260
taccactga                                                          7269
```

<210> SEQ ID NO 13
<211> LENGTH: 511
<212> TYPE: PRT
<213> ORGANISM: Vesicular stomatitis virus

<400> SEQUENCE: 13

```
Met Lys Cys Leu Leu Tyr Leu Ala Phe Leu Phe Ile Gly Val Asn Cys
1               5                   10                  15

Lys Phe Thr Ile Val Phe Pro His Asn Gln Lys Gly Asn Trp Lys Asn
            20                  25                  30

Val Pro Ser Asn Tyr His Tyr Cys Pro Ser Ser Ser Asp Leu Asn Trp
        35                  40                  45

His Asn Asp Leu Ile Gly Thr Ala Leu Gln Val Lys Met Pro Lys Ser
    50                  55                  60

His Lys Ala Ile Gln Ala Asp Gly Trp Met Cys His Ala Ser Lys Trp
```

-continued

```
             65                  70                  75                  80
Val Thr Thr Cys Asp Phe Arg Trp Tyr Gly Pro Lys Tyr Ile Thr His
                         85                  90                  95

Ser Ile Arg Ser Phe Thr Pro Ser Val Glu Gln Cys Lys Glu Ser Ile
                100                 105                 110

Glu Gln Thr Lys Gln Gly Thr Trp Leu Asn Pro Gly Phe Pro Pro Gln
            115                 120                 125

Ser Cys Gly Tyr Ala Thr Val Thr Asp Ala Glu Ala Val Ile Val Gln
130                 135                 140

Val Thr Pro His His Val Leu Val Asp Glu Tyr Thr Gly Glu Trp Val
145                 150                 155                 160

Asp Ser Gln Phe Ile Asn Gly Lys Cys Ser Asn Tyr Ile Cys Pro Thr
                    165                 170                 175

Val His Asn Ser Thr Thr Trp His Ser Asp Tyr Lys Val Lys Gly Leu
                180                 185                 190

Cys Asp Ser Asn Leu Ile Ser Met Asp Ile Thr Phe Phe Ser Glu Asp
            195                 200                 205

Gly Glu Leu Ser Ser Leu Gly Lys Glu Gly Thr Gly Phe Arg Ser Asn
        210                 215                 220

Tyr Phe Ala Tyr Glu Thr Gly Gly Lys Ala Cys Lys Met Gln Tyr Cys
225                 230                 235                 240

Lys His Trp Gly Val Arg Leu Pro Ser Gly Val Trp Phe Glu Met Ala
                    245                 250                 255

Asp Lys Asp Leu Phe Ala Ala Ala Arg Phe Pro Glu Cys Pro Glu Gly
                260                 265                 270

Ser Ser Ile Ser Ala Pro Ser Gln Thr Ser Val Asp Val Ser Leu Ile
            275                 280                 285

Gln Asp Val Glu Arg Ile Leu Asp Tyr Ser Leu Cys Gln Glu Thr Trp
        290                 295                 300

Ser Lys Ile Arg Ala Gly Leu Pro Ile Ser Pro Val Asp Leu Ser Tyr
305                 310                 315                 320

Leu Ala Pro Lys Asn Pro Gly Thr Gly Pro Ala Phe Thr Ile Ile Asn
                    325                 330                 335

Gly Thr Leu Lys Tyr Phe Glu Thr Arg Tyr Ile Arg Val Asp Ile Ala
                340                 345                 350

Ala Pro Ile Leu Ser Arg Met Val Gly Met Ile Ser Gly Thr Thr Thr
            355                 360                 365

Glu Arg Glu Leu Trp Asp Asp Trp Ala Pro Tyr Glu Asp Val Glu Ile
        370                 375                 380

Gly Pro Asn Gly Val Leu Arg Thr Ser Ser Gly Tyr Lys Phe Pro Leu
385                 390                 395                 400

Tyr Met Ile Gly His Gly Met Leu Asp Ser Asp Leu His Leu Ser Ser
                    405                 410                 415

Lys Ala Gln Val Phe Glu His Pro His Ile Gln Asp Ala Ala Ser Gln
                420                 425                 430

Leu Pro Asp Asp Glu Ser Leu Phe Phe Gly Asp Thr Gly Leu Ser Lys
            435                 440                 445

Asn Pro Ile Glu Leu Val Glu Gly Trp Phe Ser Ser Trp Lys Ser Ser
        450                 455                 460

Ile Ala Ser Phe Phe Phe Ile Ile Gly Leu Ile Ile Gly Leu Phe Leu
465                 470                 475                 480

Val Leu Arg Val Gly Ile His Leu Cys Ile Lys Leu Lys His Thr Lys
                    485                 490                 495
```

Lys Arg Gln Ile Tyr Thr Asp Ile Glu Met Asn Arg Leu Gly Lys
            500                 505                 510

<210> SEQ ID NO 14
<211> LENGTH: 6508
<212> TYPE: DNA
<213> ORGANISM: Artificial sequence
<220> FEATURE:
<223> OTHER INFORMATION: Plasmid encoding VSV-G

<400> SEQUENCE: 14

| | | | | | |
|---|---|---|---|---|---|
| gcggccgctc | tagagagctt | ggcccattgc | atacgttgta | tccatatcat | aatatgtaca | 60 |
| tttatattgg | ctcatgtcca | acattaccgc | catgttgaca | ttgattattg | actagttatt | 120 |
| aatagtaatc | aattacgggg | tcattagttc | atagcccata | tatggagttc | cgcgttacat | 180 |
| aacttacggt | aaatggcccg | cctggctgac | cgcccaacga | cccccgccca | ttgacgtcaa | 240 |
| taatgacgta | tgttcccata | gtaacgccaa | tagggacttt | ccattgacgt | caatgggtgg | 300 |
| agtatttacg | gtaaactgcc | cacttggcag | tacatcaagt | gtatcatatg | ccaagtacgc | 360 |
| cccctattga | cgtcaatgac | ggtaaatggc | ccgcctggca | ttatgcccag | tacatgacct | 420 |
| tatgggactt | tcctacttgg | cagtacatct | acgtattagt | catcgctatt | accatggtga | 480 |
| tgcggttttg | gcagtacatc | aatgggcgtg | gatagcggtt | tgactcacgg | ggatttccaa | 540 |
| gtctccaccc | cattgacgtc | aatgggagtt | tgttttggca | ccaaaatcaa | cgggactttc | 600 |
| caaaatgtcg | taacaactcc | gccccattga | cgcaaatggg | cggtaggcgt | gtacggtggg | 660 |
| aggtctatat | aagcagagct | cgtttagtga | accgtcagat | cgcctggaga | cgccatccac | 720 |
| gctgttttga | cctccataga | agacaccggg | accgatccag | cctccggtcg | accgatcctg | 780 |
| agaacttcag | ggtgagtttg | ggacccttga | ttgttctttc | ttttttcgct | attgtaaaat | 840 |
| tcatgttata | tggagggggc | aaagttttca | gggtgttgtt | tagaatggga | agatgtccct | 900 |
| tgtatcacca | tggaccctca | tgataatttt | gtttctttca | ctttctactc | tgttgacaac | 960 |
| cattgtctcc | tcttattttc | ttttcatttt | ctgtaacttt | tcgttaaac | tttagcttgc | 1020 |
| atttgtaacg | aatttttaaa | ttcacttttg | tttatttgtc | agattgtaag | tactttctct | 1080 |
| aatcactttt | ttttcaaggc | aatcagggta | tattatattg | tacttcagca | cagttttaga | 1140 |
| gaacaattgt | tataattaaa | tgataaggta | gaatatttct | gcatataaat | ctggctggc | 1200 |
| gtggaaatat | tcttattggt | agaaacaact | acaccctggt | catcatcctg | cctttctctt | 1260 |
| tatggttaca | atgatataca | ctgtttgaga | tgaggataaa | atactctgag | tccaaaccgg | 1320 |
| gcccctctgc | taaccatgtt | catgccttct | tctctttcct | acagctcctg | gcaacgtgc | 1380 |
| tggttgttgt | gctgtctcat | cattttggca | agaattcct | cgacggatcc | ctcgaggaat | 1440 |
| tctgacacta | tgaagtgcct | tttgtactta | gccttttat | tcattggggt | gaattgcaag | 1500 |
| ttcaccatag | ttttccaca | aaccaaaaa | ggaaactgga | aaatgttcc | ttctaattac | 1560 |
| cattattgcc | cgtcaagctc | agatttaaat | tggcataatg | acttaatagg | cacagcctta | 1620 |
| caagtcaaaa | tgcccaagag | tcacaaggct | attcaagcag | acggttggat | gtgtcatgct | 1680 |
| tccaaatggg | tcactacttg | tgatttccgc | tggtatggac | cgaagtatat | aacacattcc | 1740 |
| atccgatcct | tcactccatc | tgtagaacaa | tgcaaggaaa | gcattgaaca | aacgaaacaa | 1800 |
| ggaacttggc | tgaatccagg | cttccctcct | caaagttgtg | gatatgcaac | tgtgacggat | 1860 |
| gccgaagcag | tgattgtcca | ggtgactcct | caccatgtgc | tggttgatga | atacacagga | 1920 |
| gaatggggttg | attcacagtt | catcaacgga | aaatgcagca | attacatatg | ccccactgtc | 1980 |

```
cataactcta caacctggca ttctgactat aaggtcaaag ggctatgtga ttctaacctc    2040
atttccatgg acatcacctt cttctcagag gacggagagc tatcatccct gggaaaggag    2100
ggcacagggt tcagaagtaa ctactttgct tatgaaactg gaggcaaggc ctgcaaaatg    2160
caatactgca agcattgggg agtcagactc ccatcaggtg tctggttcga gatggctgat    2220
aaggatctct tgctgcagc cagattccct gaatgcccag aagggtcaag tatctctgct     2280
ccatctcaga cctcagtgga tgtaagtcta attcaggacg ttgagaggat cttggattat    2340
tccctctgcc aagaaacctg agcaaaatc agagcgggtc ttccaatctc tccagtggat     2400
ctcagctatc ttgctcctaa aaacccagga accggtcctg cttcaccat aatcaatggt     2460 accctaaaat actttgagac cagatacatc agagtcgata ttgctgctcc aatcctctca    2520
agaatggtcg gaatgatcag tggaactacc acagaaaggg aactgtggga tgactgggca    2580
ccatatgaag acgtggaaat tggacccaat ggagttctga ggaccagttc aggatataag    2640
tttcctttat acatgattgg acatggtatg ttggactccg atcttcatct tagctcaaag    2700
gctcaggtgt tcgaacatcc tcacattcaa gacgctgctt cgcaacttcc tgatgatgag    2760
agtttatttt ttggtgatac tgggctatcc aaaaatccaa tcgagcttgt agaaggttgg    2820
ttcagtagtt ggaaaagctc tattgcctct ttttctttta tcatagggtt aatcattgga    2880
ctattcttgg ttctccgagt tggtatccat ctttgcatta aattaaagca caccaagaaa    2940
agacagattt atacagacat agagatgaac cgacttggaa agtaactcaa atcctgcaca    3000
acagattctt catgtttgga ccaaatcaac ttgtgatacc atgctcaaag aggcctcaat    3060
tatatttgag ttttaatttt ttatgaaaaa aaaaaaaaa aacggaattc ctcgagggat     3120
ccgtcgagga attcactcct caggtgcagg ctgcctatca gaaggtggtg gctggtgtgg    3180
ccaatgccct ggctcacaaa taccactgag atctttttcc ctctgccaaa aattatgggg    3240
acatcatgaa gccccttgag catctgactt ctggctaata aaggaaattt attttcattg    3300
caatagtgtg ttggaatttt ttgtgtctct cactcggaag gacatatggg agggcaaatc    3360
atttaaaaca tcagaatgag tatttggttt agagtttggc aacatatgcc catatgctgg    3420
ctgccatgaa caaaggttgg ctataaagag gtcatcagta tatgaaacag cccctgctg    3480 tccattcctt attccataga aaagccttga cttgaggtta gattttttt atattttgtt     3540 ttgtgttatt ttttctttta acatcccta aattttcctt acatgtttta ctagccagat    3600
ttttcctcct ctcctgacta ctcccagtca tagctgtccc tcttctctta tggagatccc    3660
tcgacggatc ggccgcaatt cgtaatcatg tcatagctgt ttcctgtgtg aaattgttat    3720
ccgctcacaa ttccacacaa catacgagcc ggaagcataa agtgtaaagc ctggggtgcc    3780
taatgagtga gctaactcac attaattgcg ttgcgctcac tgcccgcttt ccagtcggga    3840
aacctgtcgt gccagctgca ttaatgaatc ggccaacgcg cggggagagg cggtttgcgt    3900
attgggcgct cttccgcttc ctcgctcact gactcgctgc gctcggtcgt tcggctgcgg    3960
cgagcggtat cagctcactc aaaggcggta atacggttat ccacagaatc aggggataac    4020
gcaggaaaga acatgtgagc aaaaggccag caaaaggcca ggaaccgtaa aaaggccgcg    4080
ttgctggcgt ttttccatag gctccgcccc cctgacgagc atcacaaaaa tcgacgctca    4140
agtcagaggt ggcgaaaccc gacaggacta taaagatacc aggcgtttcc ccctggaagc    4200
tccctcgtgc gctctcctgt tccgaccctg ccgcttaccg gatacctgtc cgcctttctc    4260
ccttcgggaa gcgtggcgct ttctcatagc tcacgctgta ggtatctcag ttcggtgtag    4320
```

```
gtcgttcgct ccaagctggg ctgtgtgcac gaaccccccg ttcagcccga ccgctgcgcc    4380
ttatccggta actatcgtct tgagtccaac ccggtaagac acgacttatc gccactggca    4440
gcagccactg gtaacaggat tagcagagcg aggtatgtag gcggtgctac agagttcttg    4500
aagtggtggc ctaactacgg ctacactaga agaacagtat ttggtatctg cgctctgctg    4560
aagccagtta ccttcggaaa aagagttggt agctcttgat ccggcaaaca aaccaccgct    4620
ggtagcggtg gtttttttgt ttgcaagcag cagattacgc gcagaaaaaa aggatctcaa    4680
gaagatcctt tgatcttttc tacggggtct gacgctcagt ggaacgaaaa ctcacgttaa    4740
gggattttgg tcatgagatt atcaaaaagg atcttcacct agatcctttt aaattaaaaa    4800
tgaagtttta aatcaatcta agtatatat gagtaaactt ggtctgacag ttaccaatgc     4860
ttaatcagtg aggcacctat ctcagcgatc tgtctatttc gttcatccat agttgcctga    4920
ctccccgtcg tgtagataac tacgatacgg gagggcttac catctggccc cagtgctgca    4980
atgataccgc gagacccacg ctcaccggct ccagatttat cagcaataaa ccagccagcc    5040
ggaagggccg agcgcagaag tggtcctgca actttatccg cctccatcca gtctattaat    5100
tgttgccggg aagctagagt aagtagttcg ccagttaata gtttgcgcaa cgttgttgcc    5160
attgctacag gcatcgtggt gtcacgctcg tcgtttggta tggcttcatt cagctccggt    5220
tcccaacgat caaggcgagt tacatgatcc cccatgttgt gcaaaaaagc ggttagctc    5280 cttcggtcct ccgatcgttg tcagaagtaa gttggccgca gtgttatcac tcatggttat    5340
ggcagcactg cataattctc ttactgtcat gccatccgta agatgctttt ctgtgactgg    5400
tgagtactca accaagtcat tctgagaata gtgtatgcgg cgaccgagtt gctcttgccc    5460
ggcgtcaata cgggataata ccgcgccaca tagcagaact ttaaaagtgc tcatcattgg    5520
aaaacgttct cggggcgaaa actctcaag gatcttaccg ctgttgagat ccagttcgat    5580
gtaacccact cgtgcaccca actgatcttc agcatctttt actttcacca gcgtttctgg    5640
gtgagcaaaa acaggaaggc aaaatgccgc aaaaaaggga ataagggcga cacggaaatg    5700
ttgaatactc atactcttcc tttttcaata ttattgaagc atttatcagg gttattgtct    5760
catgagcgga tacatatttg aatgtattta gaaaaataaa caaatagggg ttccgcgcac    5820
atttccccga aaagtgccac ctaaattgta agcgttaata ttttgttaaa attcgcgtta    5880
aatttttgtt aaatcagctc attttttaac caataggccg aaatcggcaa aatcccttat    5940
aaatcaaaag aatagaccga gatagggttg agtgttgttc cagtttggaa caagagtcca    6000
ctattaaaga acgtggactc caacgtcaaa gggcgaaaaa ccgtctatca gggcgatggc    6060
ccactacgtg aaccatcacc ctaatcaagt tttttggggt cgaggtgccg taaagcacta    6120
aatcggaacc ctaaagggag cccccgattt agagcttgac ggggaaagcc ggcgaacgtg    6180
gcgagaaagg aagggaagaa agcgaaagga gcgggcgcta gggcgctggc aagtgtagcg    6240
gtcacgctgc gcgtaaccac cacacccgcc gcgcttaatg cgccgctaca gggcgcgtcc    6300
cattcgccat tcaggctgcg caactgttgg gaagggcgat cggtgcgggc ctcttcgcta    6360
ttacgccagc tggcgaaagg gggatgtgct gcaaggcgat taagttgggt aacgccaggg    6420
ttttcccagt cacgacgttg taaaacgacg gccagtgagc gcgcgtaata cgactcacta    6480
tagggcgaat tggagctcca ccgcggtg                                      6508
```

<210> SEQ ID NO 15
<211> LENGTH: 7213
<212> TYPE: DNA
<213> ORGANISM: Artificial sequence -continued
<220> FEATURE:
<223> OTHER INFORMATION: Plasmid encoding a fusion of TPO and HA

<400> SEQUENCE: 15

```
gcggccggcc gctctagaga gcttggccca ttgcatacgt tgtatccata tcataatatg 60
tacatttata ttggctcatg tccaacatta ccgccatgtt gacattgatt attgactagt 120
tattaatagt aatcaattac ggggtcatta gttcatagcc catatatgga gttccgcgtt 180
acataactta cggtaaatgg cccgcctggc tgaccgccca acgacccccg cccattgacg 240
tcaataatga cgtatgttcc catagtaacg ccaataggga ctttccattg acgtcaatgg 300
gtggagtatt tacggtaaac tgcccacttg gcagtacatc aagtgtatca tatgccaagt 360
acgcccccta ttgacgtcaa tgacggtaaa tggcccgcct ggcattatgc ccagtacatg 420
accttatggg actttcctac ttggcagtac atctacgtat tagtcatcgc tattaccatg 480
gtgatgcggt tttggcagta catcaatggg cgtggatagc ggtttgactc acggggattt 540
ccaagtctcc accccattga cgtcaatggg agtttgtttt ggcaccaaaa tcaacgggac 600
tttccaaaat gtcgtaacaa ctccgcccca ttgacgcaaa tgggcggtag gcgtgtacgg 660
tgggaggtct atataagcag agctcgttta gtgaaccgtc agatcgcctg gagacgccat 720
ccacgctgtt ttgacctcca tagaagacac cgggaccgat ccagcctccg gtcgaccgat 780
cctgagaact tcagggtgag tttggggacc cttgattgtt ctttcttttt cgctattgta 840
aaattcatgt tatatggagg gggcaaagtt ttcagggtgt tgtttagaat gggaagatgt 900
cccttgtatc accatggacc ctcatgataa ttttgtttct ttcactttct actctgttga 960
caaccattgt ctcctcttat tttcttttca ttttctgtaa ctttttcgtt aaactttagc 1020
ttgcatttgt aacgaatttt taaattcact tttgtttatt tgtcagattg taagtacttt 1080
ctctaatcac ttttttttca aggcaatcag ggtatattat attgtacttc agcacagttt 1140
tagagaacaa ttgttataat taaatgataa ggtagaatat ttctgcatat aaattctggc 1200
tggcgtggaa atattcttat tggtagaaac aactacaccc tggtcatcat cctgcctttc 1260
tctttatggt tacaatgata tacactgttt gagatgagga taaaatactc tgagtccaaa 1320
ccgggcccct ctgctaacca tgttcatgcc ttcttctctt tcctacagct cctgggcaac 1380
gtgctggttg ttgtgctgtc tcatcatttt ggcaaagaat tctagactga catggcgcgt 1440
tcaacgctct caaaacccct taaaaataag gttaacccgc gaggcccccct aatcccctta 1500
attcttctga tgctcagagg ggtcagtact gcttcgcccg gctccagtgc ggcccagccg 1560
gccagcccgg ctcctcctgc ttgtgacctc cgagtcctca gtaaactgct tcgtgactcc 1620
catgtccttc acagcagact gagccagtgc ccagaggttc accctttgcc tacacctgtc 1680
ctgctgcctg ctgtggactt tagcttggga gaatggaaaa cccagatgga ggagaccaag 1740
gcacaggaca ttctgggagc agtgaccctt ctgctggagg gagtgatggc agcacgggga 1800
caactgggac ccacttgcct ctcatccctc ctggggcagc tttctggaca ggtccgtctc 1860
ctccttgggg ccctgcagag cctccttgga acccagcttc ctccacaggg caggaccaca 1920
gctcacaagg atcccaatgc catcttcctg agcttccaac acctgctccg aggaaaggtg 1980
cgtttcctga tgcttgtagg agggtccacc ctctgcgtca ggcgggcccc acccaccaca 2040
gctgtcccca gcagaacctc tctagtcctc acactggcgg ccgcaatcga gggaaggcaa 2100
gaccttccag gaaatgacaa cagcgacaaa atttgtcttg gacatcatgc tgtatcaaat 2160
ggcaccaaag taaacacact cactgagaga ggagtagaag ttgtcaatgc aacggaaaca 2220
```

```
gtggagcgga caaacatccc caaaatttgc tcaaaaggga aaagaaccac tgatcttggc    2280
caatgcggac tgttagggac cattaccgga ccacctcaat gcgaccaatt tctagaattt    2340
tcagctgatc taataatcga gagacgagaa ggaaatgatg tttgttaccc ggggaagttt    2400
gttaatgaag aggcattgcg acaaatcctc agaggatcag gtgggattga caaagaaaca    2460
atgggattca catatagtgg aataaggacc aacggaacaa ctagtgcatg tagaagatca    2520
gggtcttcat tctatgcaga aatggagtgg ctcctgtcaa atacagacaa tgcttctttc    2580
ccacaaatga caaaatcata caaaaacaca aggagagaat cagctctgat agtatgggga    2640
atccaccatt caggatcaac caccgaacag accaaactat atgggagtgg aaataaactg    2700
ataacagtcg ggagttccaa atatcatcaa tcttttgtgc cgagtccagg aacacgaccg    2760
cagataaatg gccagtccgg acggattgat tttcattggt tgatcttgga tcccaatgat    2820
acagttactt ttagtttcaa tgggcttc atagctccaa atcgtgccag cttcttgagg    2880
ggaaagtcca tggggatcca gagcgatgtg caggttgatg ccaattgcga aggggaatgc    2940
taccacagtg gagggactat aacaagcaga ttgccttttc aaaacatcaa tagcagagca    3000
gttggcaaat gcccaagata tgtaaaacag gaaagtttat tattggcaac tgggatgaag    3060
aacgttcccg aaccttccaa aaaaggaaa aaaagaggcc tgtttggcgc tatagcaggg    3120
tttattgaaa atggttggga aggtctggtc gacgggtggt acggtttcag gcatcagaat    3180
gcacaaggag aaggaactgc agcagactac aaaagcaccc aatcggcaat tgatcagata    3240
accggaaagt taaatagact cattgagaaa accaaccagc aatttgagct aatagataat    3300
gaattcactg aggtggaaaa gcagattggc aatttaatta ctggaccaa agactccatc    3360 acagaagtat ggtcttacaa tgctgaactt attgtggcaa tggaaaacca gcacactatt    3420
gatttggctg attcagagat gaacaggctg tatgagcgag tgaggaaaca attaagggaa    3480
aatgctgaag aggatggtac tggttgcttt gaaatttttc ataaatgtga cgatgattgt    3540
atggctagta taaggaacaa tacttatgat cacagcaaat acagaagaa agcgatgcaa    3600 aatagaatac aaattgaccc agtcaaattg agtagtggct acaaagatgt gatactttgg    3660
tttagcttcg gggcatcatg cttttttgctt cttgccattg caatgggcct tgtttttcata    3720 tgtgtgaaga acggaaacat gcggtgcact atttgtatat aagtttggaa aaaacacccc    3780
ttgtttctac tctctagagg atccccgggc gcgaacgtgg aagatccgtc gaggaattca    3840
ctcctcaggt gcaggctgcc tatcagaagg tggtggctgg tgtggccaat gccctggctc    3900
acaaatacca ctgagatctt tttccctctg ccaaaaatta tggggacatc atgaagcccc    3960
ttgagcatct gacttctggc taataaagga aatttatttt cattgcaata gtgtgttgga    4020
attttttgtg tctctcactc ggaaggacat atgggagggc aaatcattta aaacatcaga    4080
atgagtattt ggtttagagt ttggcaacat atgcccatat gctggctgcc atgaacaaag    4140
gttggctata aagaggtcat cagtatatga aacagccccc tgctgtccat tccttattcc    4200
atagaaaagc cttgacttga ggttagattt ttttatatt ttgttttgtg ttattttttt    4260
ctttaacatc cctaaaattt tccttacatg ttttactagc cagatttttc ctcctctcct    4320
gactactccc agtcatagct gtccctcttc tcttatggag atccctcgac ggatcggccg    4380
caattcgtaa tcatgtcata gctgtttcct gtgtgaaatt gttatccgct cacaattcca    4440
cacaacatac gagccggaag cataaagtgt aaagcctggg gtgcctaatg agtgagctaa    4500
ctcacattaa ttgcgttgcg ctcactgccc gctttccagt cggaaacct gtcgtgccag    4560 ctgcattaat gaatcggcca acgcgcgggg agaggcggtt tgcgtattgg gcgctcttcc    4620
```

```
gcttcctcgc tcactgactc gctgcgctcg gtcgttcggc tgcggcgagc ggtatcagct    4680
cactcaaagg cggtaatacg gttatccaca gaatcagggg ataacgcagg aaagaacatg    4740
tgagcaaaag gccagcaaaa ggccaggaac cgtaaaaagg ccgcgttgct ggcgtttttc    4800
cataggctcc gcccccctga cgagcatcac aaaaatcgac gctcaagtca gaggtggcga    4860
aacccgacag gactataaag ataccaggcg tttccccctg gaagctccct cgtgcgctct    4920
cctgttccga ccctgccgct taccggatac ctgtccgcct ttctcccttc gggaagcgtg    4980
gcgctttctc atagctcacg ctgtaggtat ctcagttcgg tgtaggtcgt tcgctccaag    5040
ctgggctgtg tgcacgaacc ccccgttcag cccgaccgct gcgccttatc cggtaactat    5100
cgtcttgagt ccaacccggt aagacacgac ttatcgccac tggcagcagc cactggtaac    5160
aggattagca gagcgaggta tgtaggcggt gctacagagt tcttgaagtg gtggcctaac    5220
tacggctaca ctagaagaac agtatttggt atctgcgctc tgctgaagcc agttaccttc    5280
ggaaaaagag ttggtagctc ttgatccggc aaacaaacca ccgctggtag cggtggtttt    5340
tttgtttgca agcagcagat tacgcgcaga aaaaaggat ctcaagaaga tcctttgatc    5400
ttttctacgg ggtctgacgc tcagtggaac gaaaactcac gttaagggat tttggtcatg    5460
agattatcaa aaaggatctt cacctagatc cttttaaatt aaaaatgaag ttttaaatca    5520
atctaaagta tatatgagta aacttggtct gacagttacc aatgcttaat cagtgaggca    5580
cctatctcag cgatctgtct atttcgttca tccatagttg cctgactccc cgtcgtgtag    5640
ataactacga tacgggaggg cttaccatct ggccccagtg ctgcaatgat accgcgagac    5700
ccacgctcac cggctccaga tttatcagca ataaccagc cagccggaag ggccgagcgc    5760
agaagtggtc ctgcaacttt atccgcctcc atccagtcta ttaattgttg ccgggaagct    5820
agagtaagta gttcgccagt taatagtttg cgcaacgttg ttgccattgc tacaggcatc    5880
gtggtgtcac gctcgtcgtt tggtatggct tcattcagct ccggttccca acgatcaagg    5940
cgagttacat gatccccat gttgtgcaaa aaagcgggtt agctccttcg gtcctccgat    6000
cgttgtcaga agtaagttgg ccgcagtgtt atcactcatg gttatggcag cactgcataa    6060
ttctcttact gtcatgccat ccgtaagatg cttttctgtg actggtgagt actcaaccaa    6120
gtcattctga aatagtgta tgcggcgacc gagttgctct tgcccggcgt caatacggga    6180
taataccgcg ccacatagca gaactttaaa agtgctcatc attggaaaac gttcttcggg    6240
gcgaaaactc tcaaggatct taccgctgtt gagatccagt tcgatgtaac ccactcgtgc    6300
acccaactga tcttcagcat cttttacttt caccagcgtt tctgggtgag caaaaacagg    6360
aaggcaaaat gccgcaaaaa agggaataag ggcgacacgg aaatgttgaa tactcatact    6420 cttcctttt caatattatt gaagcattta tcagggttat tgtctcatga gcggatacat    6480
atttgaatgt atttagaaaa ataaacaaat aggggttccg cgcacatttc cccgaaaagt    6540
gccacctaaa ttgtaagcgt taatattttg ttaaaattcg cgttaaattt ttgttaaatc    6600
agctcatttt ttaaccaata ggccgaaatc ggcaaaatcc cttataaatc aaaagaatag    6660
accgagatag ggttgagtgt tgttccagtt tggaacaaga gtccactatt aaagaacgtg    6720
gactccaacg tcaaagggcg aaaaaccgtc tatcagggcg atggcccact acgtgaacca    6780
tcaccctaat caagtttttt ggggtcgagg tgccgtaaag cactaaatcg aaccctaaa    6840 gggagccccc gatttagagc ttgacgggga agccggcga acgtggcgag aaaggaaggg    6900
aagaaagcga aaggagcggg cgctagggcg ctggcaagtg tagcggtcac gctgcgcgta    6960
```

```
accaccacac ccgccgcgct taatgcgccg ctacagggcg cgtcccattc gccattcagg    7020
ctgcgcaact gttgggaagg gcgatcggtg cgggcctctt cgctattacg ccagctggcg    7080 aaaggggat  gtgctgcaag gcgattaagt tgggtaacgc cagggttttc ccagtcacga    7140
cgttgtaaaa cgacggccag tgagcgcgcg taatacgact cactataggg cgaattggag    7200
ctccaccgcg gtg                                                       7213
```

VECTOR PARTICLES FOR TARGETING CD34+ CELLS

CROSS-REFERENCE TO RELATED APPLICATIONS

This application is a continuation of U.S. application Ser. No. 12/670,479, having a filing date of Jun. 11, 2010, which is a 371 application of PCT/EP2008/059674, filed Jul. 23, 2008, all of said applications being incorporated herein by reference.

BACKGROUND OF THE INVENTION

The present invention relates to vector particles intended for the specific delivery of biological material to cells.

For the correction by gene therapy of many inherited or acquired defects of the hematopoietic system, the therapeutic gene must be delivered to cells able both to self-renew and to differentiate into all hematopoietic lineages. As such, these gene therapies must be targeted to the "right" cells, i.e. hematopoietic stem cells (HSCs), without modifying their properties. The population of choice for targeting HSCs is constituted of CD34+ progenitor cells, which are particularly enriched in these stem cells. However, CD34+ cells only represent 0.001% of the total blood cells for instance. Accordingly, to avoid the cumbersome steps of cell extraction, culture in the presence of multiple growth factors or transduction adjuvants, and infusion into the patient, the vector particles have to display a very high specificity towards CD34+ cells, in order to allow transduction of CD34+ cells in non-purified bodily samples, such as blood samples, or to ensure an efficient in vivo transduction of CD34+ cells despite dilution of the vector particles.

Thus, Sandrin et al. (2002) *Blood* 100:823-832 have devised Simian Immunodeficiency Virus (SIV)-derived vector particles which display a chimeric envelope glycoprotein, RDTR, constituted of the fusion of the transmembrane and extracellular domains of the feline endogenous RD114 virus envelope glycoprotein and the cytoplasmic domain of the Murine Leukemia Virus-A envelope glycoprotein. Such vector particles are also disclosed in WO 03/91442. When using a transduction adjuvant, such as RETRONECTIN®, the transduction rate obtained using vector particles displaying the chimeric RDTR protein is of approximately the same rate as that observed with SIV-derived vector particles displaying the Vesicular Stomatitis Virus (VSV) G envelope glycoprotein. However, in the absence of transduction adjuvant, the RDTR vector particles exhibit a much lower transduction of isolated CD34+ cells than vectors displaying the VSV-G glycoprotein. Besides, no particular selectivity towards CD34+ cells has been shown to be associated to RDTR, since vector particles displaying this chimeric protein transduce CD34+ cells and peripheral blood lymphocytes with approximately the same efficiency.

In another attempt at targeting CD34+ cells, Verhoeyen et al. (2005) *Blood* 106:3386-3395 have devised HIV-1-derived vector particles which display the VSV-G envelope glycoprotein and so-called early acting cytokines, namely Thrombopoietin (TPO) and Stem Cell Factor (SCF). The authors have thus shown that these vector particles provided for efficient transduction of isolated CD34+ cells. However, no targeting specificity of these vector particles could be evidenced.

Accordingly, it is an object of the present invention to provide vector particles which are more efficient than those of the prior art at specifically targeting CD34+ cells.

SUMMARY OF THE INVENTION

The present invention arises from the discovery, by the inventors, that the co-display of RDTR and SCF on HIV-derived vector particles had unexpected synergic effects on the efficiency and the specificity of transduction of CD34+ cells. Advantageously, such vector particles are not dependant on RETRONECTIN® to achieve transduction, can effect efficient transduction at low dosage, and are capable to transduce CD34+ cells in fresh whole blood.

Thus, the present invention relates to a vector particle for transferring biological material into cells, wherein said vector particle comprises at least:
- a first protein which comprises the transmembrane and extracellular domains of the feline endogenous RD114 virus envelope glycoprotein, and
- a second protein which comprises a ligand of the c-Kit receptor.

The present invention also relates to the use of (i) a first nucleic acid comprising a sequence encoding a first protein as defined above and of (ii) a second nucleic acid comprising a sequence encoding a second protein as defined above, for preparing a vector particle for transferring biological material into cells and in particular for preparing a vector particle as defined above.

The present invention also relates to a method for preparing a vector particle for transferring biological material into cells and in particular for preparing a vector particle as defined above, wherein (i) a first nucleic acid comprising a sequence encoding a first protein as defined above and (ii) a second nucleic acid comprising a sequence encoding a second protein as defined above, are transferred in a producer cell, and the vector particle is recovered from said producer cell.

The present invention also relates to a medicament comprising a vector particle as defined above as active ingredient.

The present invention also relates to a method for treating an individual in need of gene therapy, wherein a therapeutically effective amount of a vector particle as defined above is administered to the individual.

The present invention further relates to the use of a vector particle as defined above, for transferring the biological material into cells ex vivo.

The present invention also relates to a method for preparing cells intended for treating an individual, wherein cells to be administered to the individual are contacted with a vector particle as defined above.

The present invention also relates to a method for treating an individual in need of gene therapy, wherein in a first step cells to be administered to the individual are contacted with a vector particle as defined above and in a second step said cells are administered to the individual.

The present invention also relates to a protein represented by SEQ ID NO: 4.

The present invention also relates to a nucleic acid encoding a protein of sequence SEQ ID NO: 4.

DETAILED DESCRIPTION OF THE INVENTION

Figure 1:
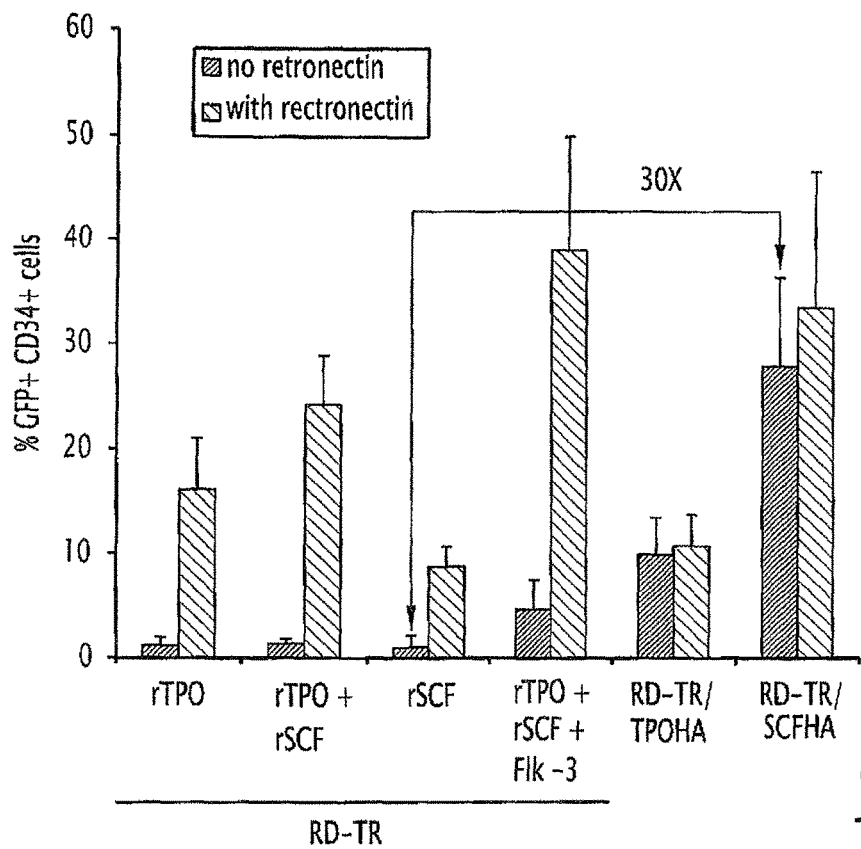
FIG. 1 represents the percentage of CD34+ cells (vertical axis) transduced by GFP-encoding HIV-derived vector particles displaying RDTR only, in the presence of recombinant TPO (10 ng/ml) or recombinant SCF (50 ng/ml), or vector particles displaying RDTR and TPOHA, or RDTR and SCFHA, in the presence (widely hatched bars) or absence (closely hatched bars) of RETRONECTIN®.

As intended herein, "vector particle" denotes any particle liable to display the first protein and the second protein at its surface and to reversibly bind to a biological material.

It is preferred that such a vector particle is a viral vector particle, in particular a lentiviral vector particle, such as a lentiviral vector particle selected from the group consisting of Human Immunodeficiency Virus (HIV), e.g. HIV-1 or HIV-2, and Simian Immunodeficiency Virus (SIV).

Lentiviral vector particles are well-known to the man skilled in the art and are notably described in Naldini et al. (2000) *Adv. Virus Res.* 55:599-609 and Negre et al. (2002) *Biochimie* 84:1161-1171. Usually, lentiviral vector particles according to the invention comprise at least the following components: (i) an envelope component, which is constituted of a phospholipidic bilayer associated to envelope proteins, wherein the envelope proteins comprise at least the above-defined first and second proteins, said envelope surrounding (ii) a core component, constituted of the association of a gag protein, said core itself surrounding (iii) genome components, usually constituted of ribonucleic acids (RNA), and (iv) an enzyme component (pol). The biological material can be present within the envelope, within the core and/or within the genome components.

Lentiviral vector particles can be readily prepared by the man skilled in the art, for example by following the general guidance provided by Sandrin at al. (2002) *Blood* 100:823-832. Briefly, the lentiviral vector particles may be generated by co-expressing the packaging elements (i.e. the core and enzyme components), the genome component and the envelope component in a so-called producer cell, e.g. 293T human embryonic kidney cells. Typically from three to four plasmids may be employed, but the number may be greater depending upon the degree to which the lentiviral components are broken up into separate units.

Generally, one plasmid encodes the core (gag) and enzymatic (pol) lentiviral components of the vector particle. The origin of the gag and pol genes gives its name to the lentiviral vector particle. For instance the expression "HIV-1-derived vector particle" usually indicates that the gag and pol genes of the vector particle are those of HIV-1. This plasmid is termed the packaging plasmid. One or several other plasmids encode the proteins which are part of the envelope. In the present case these plasmids may notably encode the first and the second protein. As will be clear to one of skill in the art, the above defined first and second nucleic acid may be either distinct or fused. Yet another plasmid encodes the genome.

As intended herein the expression "biological material" relates to one or more compounds liable to alter the structure and/or the function of a cell. Within the context of the present invention, it is preferred that the biological material is one or more nucleic acids, which in the case of lentiviral vector particles may be comprised within the genome of the vector particle. The genome typically comprises the one or more nucleic acids, preferably linked to genetic elements necessary for their expression in the target cell, such as promoters and terminators, flanked by cis-acting elements necessary for the inclusion of the genome in the core element, its reverse transcription into deoxyribonucleic acid (DNA), the import of the retrotranscribed genome into the nucleus of the target cell and the integration of the retrotranscribed genome within the genome of the target cell.

As intended herein the recipient cells for the biological material to be transferred, or target cells, relate to any cell liable to be bound by the above-defined vector particle. Where the vector particle is a lentiviral vector particle the target cell relates to any cell liable to be transduced by the vector particle. These cells usually express the c-Kit receptor which binds to the c-Kit ligand of the first protein. As such, the cells preferably targeted by the vector particle of the invention are $CD34^+$ cells, in particular human $CD34^+$ cells, and more particularly Hematopoietic Stem Cells (HSCs), notably human HSCs.

As intended herein "transferring" relates to the capacity of the vector particle to initially deliver the biological material to the membrane or the cytoplasm of the target cell, upon being bound to the target cell. After delivery, the biological material can be translocated to other compartment of the cell.

The feline endogenous RD114 virus envelope glycoprotein is notably described in Cosset et al. (1995) *J. Virol.* 69:7430-7436. By way of example, the RD114 virus envelope glycoprotein corresponds to GenBank accession number X87829. Portions of RD114 corresponding to the transmembrane and extracellular domains can be readily identified by the man skilled in the art.

As intended herein, the expression "transmembrane and extracellular domains of the feline endogenous RD114 virus envelope glycoprotein" relates to transmembrane and extracellular domains of a natural feline endogenous RD114 virus envelope glycoprotein or to any mutant thereof derived therefrom by deletion, insertion or substitution of one or several amino acids, provided that said mutant presents essentially the same properties as the transmembrane and extracellular domains of the natural feline endogenous RD114 virus envelope glycoprotein from which it derives.

As intended herein, a mutant will be said to present essentially the same properties as the transmembrane and extracellular domains of a natural feline endogenous RD114 virus envelope glycoprotein from which it derives, if, when replacing the transmembrane and extracellular domains of a natural feline endogenous RD114 virus envelope glycoprotein in a reference vector particle according to the invention carrying a first protein of sequence SEQ ID NO: 2 and a second protein of sequence SEQ ID NO: 4, the mutant-carrying vector particle presents at least 30%, preferably at least 50%, more preferably at least 75%, of the transduction of $CD34^+$ cells which can be observed with the reference vector particle. Preferably, the transduction conditions are those set forth in Example 2.

By way of example, the transmembrane and extracellular domains of the feline endogenous RD114 virus envelope glycoprotein are represented by SEQ ID NO: 5.

Preferably, the first protein comprises or consists in a fusion of the transmembrane and extracellular domains of the feline endogenous RD114 virus envelope glycoprotein and the cytoplasmic domain of a retroviral envelope glycoprotein. In this fusion it is preferred that the C-terminus of the transmembrane domain of RD114 is fused to the N-terminus of the cytoplasmic domain of a retroviral envelope glycoprotein.

More preferably, the first protein comprises or consists in a fusion of the transmembrane and extracellular domains of the feline endogenous RD114 virus envelope glycoprotein and the cytoplasmic domain of the Murine Leukemia Virus-A envelope glycoprotein. In this fusion it is preferred that the C-terminus of the transmembrane domain of RD114 is fused to the N-terminus of the cytoplasmic domain of MLV-A envelope glycoprotein.

The Murine Leukemia Virus-A envelope glycoprotein is notably described in Ott et al. (1990) *J. Virol.* 64:757-766. Preferably, the Murine Leukemia Virus-A envelope glycoprotein is that of strain 4070A. The portion of Murine Leukemia Virus-A envelope glycoprotein corresponding to the intracellular domain can be readily identified by the man skilled in the art. By way of example the intracellular domain of Murine Leukemia Virus-A envelope glycoprotein is represented by SEQ ID NO: 6.

Most preferably, the first protein is represented by SEQ ID NO: 2 and is in particular encoded by SEQ ID NO: 1. A preferred plasmid for expressing the first protein in a producer cell is represented by SEQ ID NO: 11.

The c-Kit receptor is well known to the man skilled in the art. It is notably described by Ashman (1999) *Int. J. Biochem. Cell. Biol.* 31:1037-1051. By way of example, the human c-Kit receptor is encoded by SEQ ID NO: 8. Accordingly, it is well within the reach of the man skilled in the art to identify, design or select ligands of the c-Kit receptor.

The natural ligand of the c-Kit receptor is the Stem Cell Factor (SCF) cytokine. The SCF cytokine is notably described by Ashman (1999) *Int. J. Biochem. Cell. Biol.* 31:1037-1051. As such, in the above-defined vector particle, the ligand of the c-Kit receptor is preferably the SCF cytokine. As intended herein the expression SCF cytokine relates to a natural SCF cytokine or to any mutant of a natural SCF cytokine derived from said natural SCF by deletion, insertion or substitution of one or several amino acids, wherein said mutant retains the ability of the natural SCF cytokine to bind to the c-Kit receptor. Preferably, the SCF cytokine is the human SCF cytokine. By way of example the human SCF cytokine corresponds to GenBank reference number P21583. It is most preferred that the SCF cytokine used herein is deprived of its signal peptide and of its transmembrane and cytoplasmic domain (i.e. only the extracellular domain of the SCF cytokine is used), e.g. as represented by SEQ ID NO: 9.

More preferably, the second protein of the above-defined vector particle comprises or consists in a fusion of the SCF cytokine and (i) the N-terminal domain of an hemagglutinin glycoprotein, or (ii) a retroviral envelope glycoprotein. In this fusion it is preferred that the C-terminus of SCF is fused to the N-terminus of the N-terminal domain of the hemagglutinin glycoprotein or to the N-terminus of the retroviral envelope glycoprotein.

Preferably, the hemagglutinin glycoprotein is that of an influenza virus, more preferably of the Fowl Plague Virus.

Preferably, the N-terminal domain of the hemagglutinin glycoprotein comprises or consists in the contiguous amino acids from the N-terminus of the glycoprotein to the C-terminus of the HA1 subunit.

The subunit structure of the hemagglutinin glycoprotein is well known to one of skill in the art. The Fowl Plaque Virus hemagglutinin is notably described in Hatziioannou et al. (1998) *J. Virol.* 72:5313-5317.

By way of example the N-terminal domain of the Fowl Plague Virus hemagglutinin is represented by SEQ ID NO: 10.

Preferably, in the second protein, the retroviral envelope glycoprotein is Murine Leukemia Virus-A envelope glycoprotein.

As will be apparent to anyone of skill in the art, the second protein may also preferably comprise a signal peptide intended for promoting endoplasmic reticulum translocation of the second protein. In certain cases the signal peptide can be cleaved during or after insertion in the targeted membrane. Such signal peptides are well known to the man skilled in the art and can be found, for example, at the extremities of membrane proteins. By way of example the signal peptide can be that of the Murine Leukemia Virus-A envelope glycoprotein, which can be represented by SEQ ID NO: 7.

Thus, the second protein preferably comprises or consists in a fusion of the SCF cytokine, the N-terminal domain of an hemagglutinin glycoprotein, and a signal peptide. In this fusion it is preferred that the C-terminus of the signal peptide is fused to the N-terminus of SCF, and that the C-terminus of SCF is fused to the N-terminus of the N-terminal domain of the hemagglutinin glycoprotein:

When the second protein comprises or consists in a fusion of SCF and a retroviral envelope glycoprotein, it is preferred that the C-terminus of SCF is fused to the N-terminus of the retroviral envelope glycoprotein deprived of its signal peptide, and that the N-terminus of SCF is fused to the C-terminus of a signal peptide as defined above, which is preferably the signal peptide of the retroviral envelope glycoprotein to which it is fused.

Most preferably, the second protein is represented by SEQ ID NO: 4 and is in particular encoded by SEQ ID NO: 3. A preferred plasmid for expressing the first protein in a producer cell is represented by SEQ ID NO: 12.

In a particular embodiment of the above-defined vector particle, the first protein is represented by SEQ ID NO: 2 and the second protein is represented by SEQ ID NO: 4.

In another particular embodiment, the second protein as defined above is fused to the first protein as defined above. Preferably, when the first and second proteins are fused, the second protein consists of a SCF cytokine, optionally fused to a signal peptide as defined above. More preferably, when the first and second protein are fused, the C-terminus of a signal peptide is fused to the N-terminus of a SCF cytokine, the C-terminus of the SCF cytokine is fused to the N-terminus of the extracellular domain of RD114, and the C-terminus of the transmembrane domain of RD114 is fused to the N-terminus of the cytoplasmic domain of a retroviral envelope glycoprotein.

The present invention also relates to the fused first and second proteins as defined above and to the nucleic acids which comprise sequences encoding them.

In another particular embodiment, the above-defined vector particle does not comprise the Vesicular Stomatitis Virus (VSV) G envelope glycoprotein.

The VSV-G envelope glycoprotein is notably described in Yee et al. (1994) *Methods Cell Biol.* 43:99-112. By way of example the VSV-G envelope glycoprotein is represented by SEQ ID NO: 13.

As is apparent from the foregoing, the above-defined vector particle can be used for the in vivo or ex vivo transfer of biological material to cells, in particular to CD34$^+$ cells, and among them to HSCs.

Accordingly, the vector particle is particularly indicated for treating hematopoietic cells-related diseases either by direct administration of the vector particle to the individual afflicted by such a disease, or by administering cells, in particular cells originating from the individual afflicted by such a disease, which have been contacted ex vivo with the vector particle.

In this frame, it is preferred that the vector particle is a lentiviral vector particle as defined above and/or that the target cells are transduced by one or more nucleic acids, preferably intended for treating the disease.

The vector particle would thus be indicated for treating myelosupression and neutropenias which may be caused as a result of chemotherapy, immunosuppressive therapy, infections such as AIDS, genetic disorders of hematopoietic cells, cancers and the like.

Exemplary genetic disorders of hematopoietic cells that are contemplated include sickle cell anemia, thalassemias, hemaglobinopathies, Glanzmann thrombasthenia, lysosomal storage disorders (such as Fabry disease, Gaucher disease, Niemann-Pick disease, and Wiskott-Aldrich syndrome), severe combined immunodeficiency syndromes (SCID), as well as diseases resulting from the lack of systemic production of a secreted protein, for example, coagulation factor VIII and/or IX.

In such cases, one would desire to transfer one or more nucleic acids such as globin genes, hematopoietic growth factors, which include erythropoietin (EPO), the interleukins (especially Interleukin-1, Interleukin-2, Interleukin-3, Interleukin-6, Interleukin-12, etc.) and the colony-stimulating factors (such as granulocyte colony-stimulating factor, granulocyte/macrophage colony-stimulating factor, or stem-cell colony-stimulating factor), the platelet-specific integrin αIIbβ, multidrug resistance genes, the gp91 or gp 47 genes which are defective in patients with chronic granulomatous disease (CGD), antiviral genes rendering cells resistant to infections with pathogens such as human immunodeficiency virus, genes coding for blood coagulation factors VIII or IX which are mutated in, hemophiliacs, ligands involved in T cell-mediated immune responses such as T cell antigen receptors, B cell antigen receptors (immunoglobulins), the interleukin receptor common γ chain, a combination of both T and B cell antigen receptors alone and/or in combination with single chain antibodies (ScFv), IL2, IL12, TNF, gamma interferon, CTLA4, B7 and the like, genes expressed in tumor cells such as Melana, MAGE genes (such as MAGE-1, MAGE-3), P198, PIA, gp100 etc.

Exemplary cancers are those of hematopoietic origin, for example, arising from myeloid, lymphoid or erythroid lineages, or precursor cells thereof. Exemplary myeloid disorders include, but are not limited to, acute promyeloid leukemia (APML), acute myelogenous leukemia (AML) and chronic myelogenous leukemia (CML). Lymphoid malignancies which may be treated using a vector particle as defined above include, but are not limited to acute lymphoblastic leukemia (ALL) which includes B-lineage ALL and T-lineage ALL, chronic lymphocytic leukemia (CLL), pro-lymphocytic leukemia (PLL), hairy cell leukemia (HLL) and Waldenstrom's macroglobulinemia (WM). Additional forms of malignant lymphomas contemplated as candidates for treatment utilizing the lentiviral vector particles of the present invention include, but are not limited to non-Hodgkin lymphoma and variants thereof, peripheral T-cell lymphomas, adult T-cell leukemia/lymphoma (ATL), cutaneous T-cell lymphoma (CTCL), large granular lymphocytic leukemia (LGF) and Hodgkin's disease.

Where the vector particle is used as a medicament and is administered to an individual in a therapeutic method, administration through the intravenous route or by the medullar route, in particular the femur or humerus medullar route, is preferred. For intravenous administration a unit dose from about $5.10^8$ to about $10^9$ vector particles as defined above can be used, whereas for medullar administration a unit dose from about $10^8$ to about $5.10^8$ vector particles as defined above can be used.

Where the vector particle is used ex vivo the vector particle can be contacted, preferably in vitro, either with isolated or purified cells, such as CD34+ cells, or with non-purified bodily samples.

The cells can be isolated or purified from various tissues, in particular taken from the individual, such as blood, in particular cord blood, or bone marrow.

Non-purified bodily samples can originate from the individual to be treated, and notably comprise blood samples, in particular whole cord blood samples.

The quantity of vector particle to be used for ex vivo transfers of biological material is for example from about $10^7$ to about $5.10^7$ for about $10^6$ total white blood cells (where the cells to be transduced are comprised in total white blood cells from a whole blood sample).

EXAMPLES

Example 1

Production of Lentiviral Vector Particles (LVs)

The inventors displayed two early acting cytokines, Thrombopoietin (TPO) and Stem Cell Factor (SCF), on a lentiviral vector particle (LV) surface.

A TPO truncated form of 171-amino acid long, shown to have a 3-fold higher biological activity than wild-type TPO, was fused to the N-terminus of the influenza hemagglutinin (HA) glycoprotein to form TPOHA. The second cytokine, SCF, was also fused to the N-terminus of HA glycoprotein to form SCFHA (SEQ ID NO: 4), which efficiently incorporates on LVs.

Since these chimeric HA glycoproteins demonstrated a reduced infectivity, an additional fusion competent glycoprotein was co-expressed. A chimeric feline endogenous RD114 virus envelope glycoprotein was chosen, in which the cytoplasmic tail of RD114 was exchanged for that of Murine Leukemia Virus-A (MLV-A) env glycoprotein resulting in a mutant RDTR (SEQ ID NO: 2), that allows high incorporation onto HIV as well as SIV vector particles (Sandrin et al. (2002) Blood 100:823-832).

Thus, a transfection protocol was optimized to co-display SCFHA or TPOHA with RDTR on HIV-derived lentiviral vector particles.

Briefly, $2.5.10^6$ 293T cells were seeded the day before transfection in 10 cm plates in a final volume of 10 ml DMEM. The next day these cells were cotransfected with an HIV or SIV gag-pol construct (8.6 µg) with the lentiviral gene transfer vector particle (8.6 µg) and two glycoprotein-encoding constructs selected from: a) VSV-G (1.5 µg) (SEQ ID NO: 14) or RDTR (SEQ ID NO: 11) (7 µg) and b) TPOHA (SEQ ID NO: 15) or c) SCFHA (SEQ ID NO: 12) (1.5 µg), using the Clontech calcium-phosphate transfection system. 4 µg of a neuraminidase-encoding plasmid was also co-transfected to allow efficient release of vector particle from the producer cell since the HA (SCFHA and TPOHA) envelope otherwise binds the vector particles to the producer cells because of the expression of sialic acid by the producer 293T cells. 15 h after transfection, the medium was replaced with 6 ml of fresh CeliGro® medium (CellGenix) and 36 h after transfection, vector particles were harvested, filtrated through 0.45 µm pore-sized membrane and stored at –80° C. The vector particles can be further concentrated via ultra-centrifugation or polyethylene-glycol mediated concentration at low-speed centrifugation.

Titers of $5.10^5$-$10^6$ IU/ml were thus obtained, that were comparable to RDTR single pseudotyped vector particles.

Functional co-display of TPO on TPOHA/RDTR co-displaying vector particles was demonstrated on BAF3-Mpl cells, which are dependent on TPO for survival and growth, essentially as described by Geddis et al. (2001) J. Biol. Chem. 276:34473-34479. Similarly, functional co-display of SCF on SCFHA/RDTR vector particles was confirmed since they sustained survival of BAF3-cKit cells which depend on SCF for survival (Bayle et al. (2004) J Biol. Chem. 279: 12249-12259), even at low multiplicity of infection (M.O.I.)

Example 2

Transduction of Isolated CD34+ Cells

The vector particles were first tested on the transduction of CD34+ cells isolated from human cord blood (CB). CB CD34+ cells are very immature hematopoietic cells containing hematopoietic stem cells.

Briefly, CD34+ cells were isolated by positive selection using anti-CD34+ beads (Miltenyi Biotech) from cord blood and were cultured on uncoated or RETRONECTIN® (Takara) coated plates. Subsequently, the cells were incubated with Green Fluorescent Protein (GFP) encoding HIV derived vector particles displaying RDTR, in the presence of human recombinant cytokines (TPO=10 ng/ml; SCF=50 ng/ml) (Preprotech, Rocky Hill, US), or co-displaying RDTR and TPOHA or RDTR and SCFHA, at a multiplicity of infection (M.O.I.) of 10, essentially as described by Verhoeyen et al. (2005) Blood 106:3386-3395.

As shown in FIG. 1, the resulting RDTR/SCFHA pseudotyped HIV vector particles were far more efficient in transducing cord blood-derived CD34+ cells, than the LV pseudotyped with RDTR and TPOHA, or with RDTR only in the presence of the corresponding cytokines in their soluble form. In addition, in contrast to the RDTR/SCFHA pseudotyped HIV vector particles, the RDTR-only pseudotyped vector particles are completely dependent on RETRONECTIN® for the transduction of CD34+ cells (RETRONECTIN® is a chimeric peptide of human fibronectin produced in Escherichia coli which is thought to link vector particles and target cells).

Thus, the above results indicate that an unexpected synergistic mechanism is taking place, between RDTR, allowing vector particle and cell fusion, and SCFHA, allowing specific binding and stimulation of c-Kit+/CD34+ cells, which results in the high transduction efficiency observed.

Example 3

Multiplicity of Infection for CD34+ Cells

An important issue for the in vivo use of the vector particles of the invention is that they should allow high transduction efficiency into CD34+ cells even at very low vector particle dosage, since a systemic administration of a therapeutic vector particle would result in an important dilution of vector particle concentration. Thus, the Inventors tested the minimal effective dosage of the vector particles according to the invention.

Briefly, CD34+ cells were isolated by positive selection using anti-CD34+ beads (Miltenyi Biotech) from cord blood and were cultured on uncoated culture plates (i.e. in the absence of RETRONECTIN®). Subsequently, the cells were incubated with Green Fluorescent Protein (GFP) encoding HIV derived vector particles displaying RDTR, in the presence of human recombinant cytokines (TPO=10 ng/ml; SCF=50 ng/ml), or co-displaying RDTR and TPOHA or RDTR and SCFHA at a M.O.I: of 10, 2, or 0.2, essentially as described by Verhoeyen et al. (2005) Blood 106:3386-3395. At day 3 post initiation of transduction, cells were evaluated for GFP expression by fluorescence-activated cell sorter (FACS).

Figure 2:
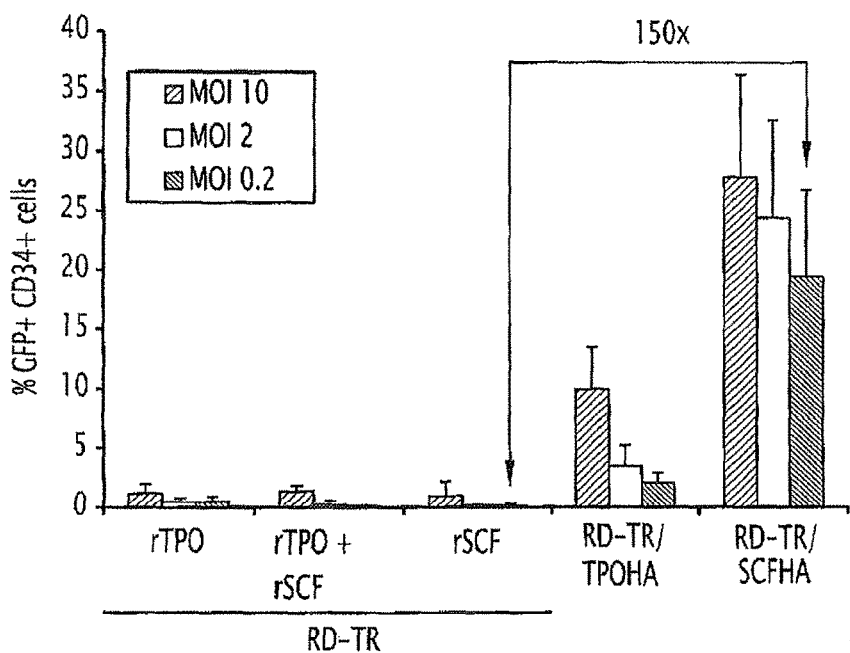
FIG. 2 represents the percentage of CD34+ cells (vertical axis) transduced by GFP-encoding HIV-derived vector particles displaying RDTR only, in the presence of recombinant TPO (10 ng/ml) or recombinant SCF (50 ng/ml), or vector particles displaying RDTR and TPOHA, or RDTR and SCFHA, at a Multiplicity Of Infection (M.O.I.) of 10 (widely hatched bars), 2 (white bars) or 0.2 (closely hatched bars) as determined on HeLa cells.

As shown in FIG. 2, the RDTR/SCFHA vector particle of the invention enabled a reduction of vector particle dosage to a M.O.I. of 0.2, without observing a significant drop in transduction efficiency of $CD34^+$ cells. Thus, a 50-fold decrease in RDTR/SCFHA vector particle dosage resulted on average only in a 1.4-fold reduction of $CD34^+$ cell transduction. In contrast, the RDTR/TPOHA vector particle resulted in a significantly lower $CD34^+$ transduction when an M.O.I. of 0.2 was used.

Example 4

RDTR/SCFHA Targets Transduction to $CD34^+$ Cells in a Peripheral Mononuclear Blood Cell Population A vector particle intended for in vivo gene therapy notably needs to be highly discriminative between target and non-target cells. Thus, after having demonstrated the ability of the vector particle according to the invention to transduce isolated $CD34^+$ cells, its selectivity was evaluated by adding vector particle to a whole peripheral blood mononuclear cell (PBMC) population at low M.O.I. In this respect, it is important to highlight that no more than 1% $CD34^+$ cells are contained in such a population.

Briefly, PBMCs were isolated from fresh cord blood by ficol gradient, as is well-known to the man skilled in the art, and cultured in the absence of RETRONECTIN®. Transduction of PBMCs was performed with Green Fluorescent Protein (GFP) encoding HIV derived vector particles displaying RDTR or VSV-G in the presence of human rSCF (50 ng/ml), or co-displaying RDTR and SCFHA or VSV-G and SCFHA, without adding exogenous cytokines, at a M.O.I. of 0.2, essentially as described by Verhoeyen et al. (2005) Blood 106:3386-3395. At day 3 post initiation of transduction, $CD34^+$ and $CD3^+$ cells were evaluated for GFP expression by fluorescence-activated cell sorter (FACS).

Figure 3:
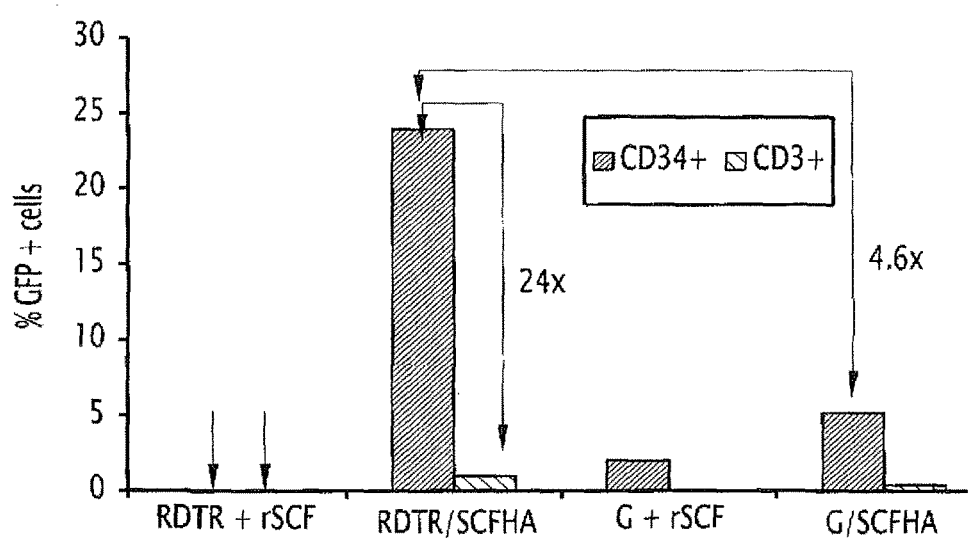
FIG. 3 represents the percentage of GFP expressing cells (vertical axis) present in a PBMC population isolated from cord blood transduced by GFP-encoding HIV-derived vector particles displaying RDTR only in the presence of recombinant SCF (50 ng/ml), RDTR and SCFHA, VSV-G only in the presence of recombinant SCF (50 ng/ml), or VSV-G and SCFHA, wherein the cells are CD34+ cells (closely hatched bars) or CD3+ cells (widely hatched bars).

As shown in FIG. 3, the RDTR/SCFHA vector particle was able to preferentially target and transduce $CD34^+$ target cells (up to 19%), in sharp contrast to the vector particle pseudotyped with RDTR only, in the presence of soluble SCF, which provided for no transduction at all, or to the VSV-G/SCFHA vector particle, which allowed a transduction level of $CD34^+$ cells of 5% at the most. Importantly, the RDTR/SCFHA vector particle allowed to transduce $CD34^+$ cells within the PBMC population at a level equivalent to that obtained for the transduction of isolated $CD34^+$ cells (compare FIGS. 2 and 3). Furthermore, the T-cell population, which make up 80% of the whole PBMC population, was very poorly transduced by the RDTR/SCFHA vector particle (FIG. 3). Worth noting, other cell lineages present in the PBMC population, such as monocytes, B-cells and NK-cells were not transduced at all.

Example 5

RDTR/SCFHA Targets Transduction to $CD34^+$ Cells in In Vivo-Like Conditions

The inventors then devised conditions as close as possible to in vivo settings for targeting gene transfer into $CD34^+$ cells. Thus, the inventors performed transduction of fresh total cord blood, which contains cells from each hematopoietic lineage: early progenitors, including Hematopoietic Stem Cells (HSCs), lymphocytes, monocytes, and erythrocytes. This allows, (i) evaluation of targeted gene transfer in the $CD34^+$ cells population, which represents only 0.001% of cells in whole blood, and (ii) exposure of the vector particle to an active human complement system, an obstacle encountered by viral vector particles in vivo.

Thus, fresh total cord blood (0.5 ml) was incubated with GFP encoding HIV vector particles pseudotyped with RDTR only or VSV-G only, in the presence of soluble SCF (50 ng/ml), or co-displaying RDTR and SCFHA or VSV-G and SCFHA, without adding exogenous cytokines, at a M.O.I. of 0.01 (calculated for the total amount of white and red blood cells present in the blood sample). After 6-8 h incubation with the vector particles, total PBMCs were separated from the blood by a ficol gradient.

Subsequently, the $CD34^+$ cells were isolated by positive selection using anti-$CD34^+$ beads (Miltenyi Biotech) and were further cultured in a serum-free medium in presence of soluble recombinant human SCF in order to sustain survival until FACS analysis.

In order to reveal possible non-target gene transfer, after removal of the $CD34^+$ cells, the residual PBMCs, consisting mainly of T-cells, were cultured in RPMI supplemented with anti-CD3 and anti-CD28 antibodies (BD Pharmingen, Le Pont de Claix, France) and recombinant human IL-2 (Preprotech Rocky Hill, US). This was done with a dual purpose: (i) to activate T-cells in order to enable transduction, since the majority of T-cells in the blood are in a quiescent state and accordingly are not permissive to lentiviral transduction, and (ii) to sustain survival of these cells until analysis. Worth noting, very stringent conditions were thus used to reveal gene transfer in the non-target T-cell, which are most probably never met in in vivo conditions. In other words the experimental settings used most probably overestimate in vivo non-specific gene transduction of T-cell. At day 4 post initiation of transduction, $CD34^+$ and $CD3^+$ cells were evaluated for GFP expression by fluorescence-activated cell sorter (FACS).

Figure 4:
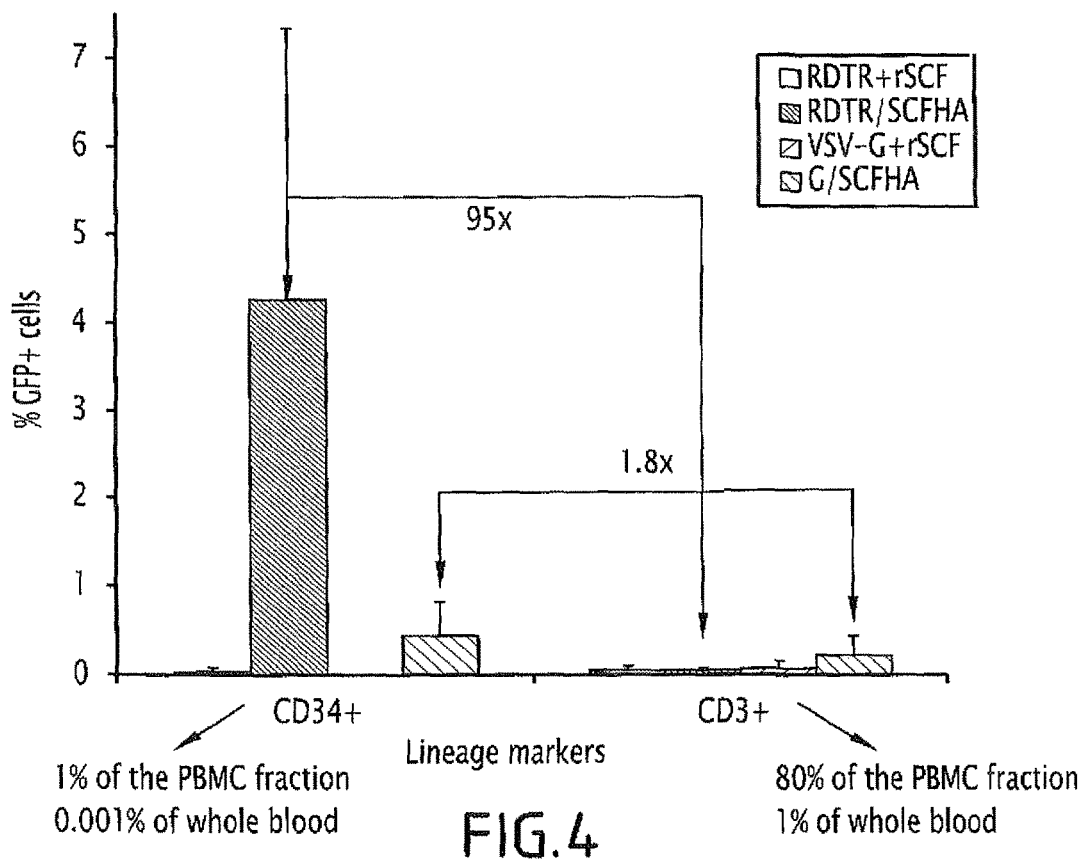
FIG. 4 represents the percentage (vertical axis) of GFP expressing CD34+ cells or CD3+ cells present in whole cord blood transduced by GFP-encoding HIV-derived vector particles displaying RDTR only in the presence of recombinant SCF (50 ng/ml) (first bar), RDTR and SCFHA (second bar), VSV-G only and recombinant SCF (50 ng/ml) (third bar), or VSV-G and SCFHA (fourth bar).

As shown in FIG. 4, the RDTR/SCFHA vector particle allowed a transduction of 4.5% $CD34^+$ cells versus 0.4% for the VSV-G/SCFHA vector particle, while transduction with vector particles displaying VSV-G only or RDTR only is negligible. Thus, the RDTR/SCFHA vector particle is 10 times more efficient than the VSV-G/SCFHA vector particle for transducing $CD34^+$ cells. In addition, the VSV-G/SCFHA vector particle readily transduced the non-target T-cell population, resulting in an 1.8 fold only selectivity for $CD34^+$ cells transduction as compared to T-cell. In contrast, the RDTR vector particle demonstrates up to 95-fold selectivity for $CD34^+$ cells as compared to T-cells. Thus, knowing that only 0.01% of the blood cells initially transduced are $CD34^+$ cells and that T-cells represent 1% of the blood cells, the RDTR/SCFHA vector particles efficiently target transduction to $CD34^+$ cells.

As regards the low transduction efficiency achieved with the VSV-G/SCFHA vector particles, it might be due to the vector's susceptibility to human complement, which, as a consequence, would impair its use in vivo.

Example 6

RDTR/SCFHA Displaying LVs Allow Gene Transfer into $hCD34^+$ Cells In Vivo

The inventors assessed targeted gene transfer into HSCs by the RDTR/SCFHA vector particles in vivo in a humanized murine model.

Briefly, full and functional reconstitution of all human haematopoietic lineages including B and T-cells was achieved in newborn Rag2$^{-/-}$; γc$^{-/-}$ Balbc mice by injection with human umbilical cord blood (UCB) CD34$^+$ cells. After 13 weeks of reconstitution the inventors detected on average 35% of human cells (hCD45$^+$) in the bone marrow of these mice (FIG. 5) of which 5 to 15% expressed hCD34.

GFP-encoding RDTR/SCFHA vector particles were concentrated by low speed centrifugation over a filtration column to obtain titers up to $5.10^8$ IU/ml. $1.10^5$ infectious units of the RDTR/SCFHA vector particles were injected into the femural bone marrow of the humanized mice from 13 week of age on.

One week after the injection, three-colour marking was performed to measure GFP expression in the different haematopoietic lineages as well as in the target hCD34$^+$ cells in the bone marrow.

Figure 5:
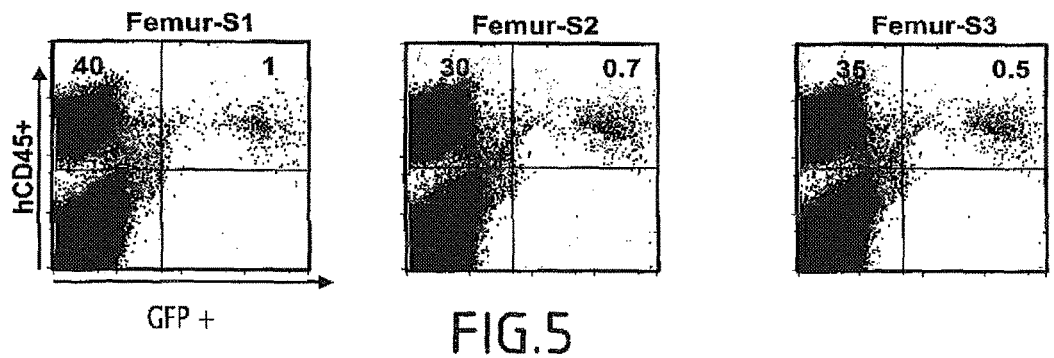
FIG. 5 represents the analysis by fluorescence-activated cell sorter (FACS) of the transduction (GFP+) of total human cells in the bone marrow. The three histograms show respectively the results obtained on three different injected mice. The cells were sorted according to hCD45 expression (hCD45+, vertical axis) and GFP expression (GFP+, horizontal axis).
Figure 6:
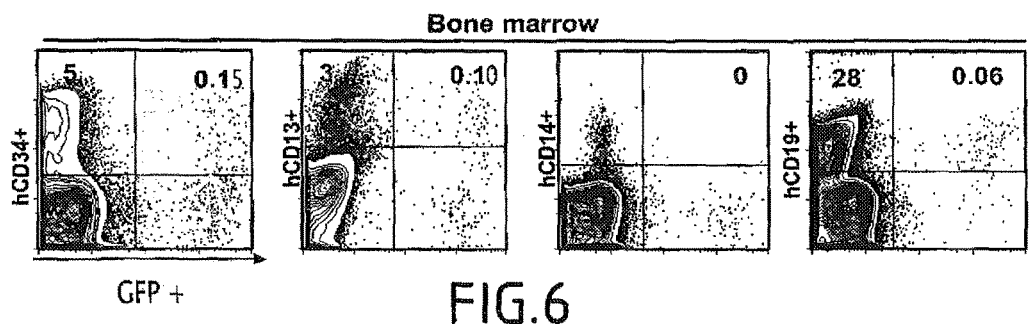
FIG. 6 represents the analysis by FACS of the transduction (GFP+) of early progenitors (hCD34+), myeloid progenitors (hCD13+), monocytes (hCD14+) and pre- and pro B-cells (hCD19+) in the bone marrow. The first histogram shows the results obtained with cells sorted according to hCD34 expression (hCD34+, vertical axis) and GFP expression (GFP+, horizontal axis). The second histogram shows the results obtained with cells sorted according to hCD13 expression (hCD13+, vertical axis) and GFP expression (horizontal axis). The third histogram shows the results obtained with cells sorted according to hCD14 expression (hCD14+, vertical axis) and GFP expression (horizontal axis). The fourth histogram shows the results obtained with cells sorted according to hCD19 expression (hCD19+, vertical axis) and GFP expression (horizontal axis).

In the flushed bone marrow the inventors detected a transduction of up to 3% of the total human cells that had colonized the marrow of the mice (FIG. 5). Taking into account that a femur contains $1.5.10^7$ cells, the inventors administered a very low vector dose (MOI=0.006). However, a selective transduction of up to 3% of early human progenitors (hCD34$^+$ cells) and of 3% of the myeloid progenitors (hCD13$^+$) in the BM was detected (FIG. 6). In contrast, monocytes and pre- and pro-B-cells were transduced to a low extent (hCD14=0%; hCD19=0.2%). These results should be explained by the fact, that one week after the injection, differentiation of hCD34$^+$ cells, including transduced hCD34$^+$ cells, into early progenitors such as hCD13$^+$ myeloid progenitors and pre- and pro-B cells may have already occurred.

Figure 7:
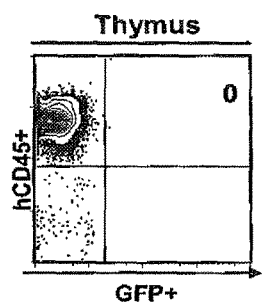
FIG. 7 represents the analysis by FACS of the transduction (GFP+) of human thymocytes in the thymus. The cells were sorted according to hCD45 expression (hCD45+, vertical axis) and GFP expression (GFP+, horizontal axis).
Figure 8:
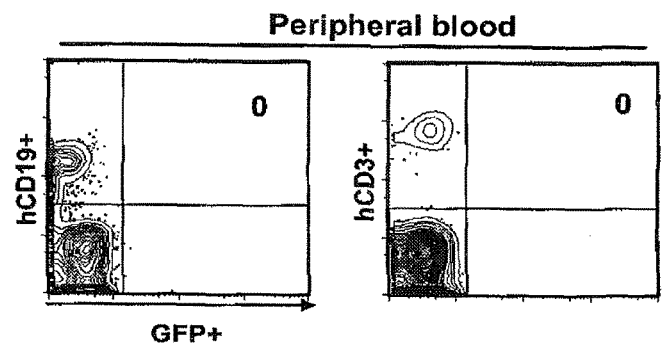
FIG. 8 represents the analysis by FACS of the transduction (GFP+) of B-cells (hCD19+) and T-cells (hCD3+) in the peripheral blood. The first histogram shows the results obtained with cells sorted according to hCD19 expression (hCD19+, vertical axis) and GFP expression (GFP+, horizontal axis). The second histogram shows the results obtained with cells sorted according to hCD3 expression (hCD3+, vertical axis) and GFP expression (horizontal axis).
Figure 9:
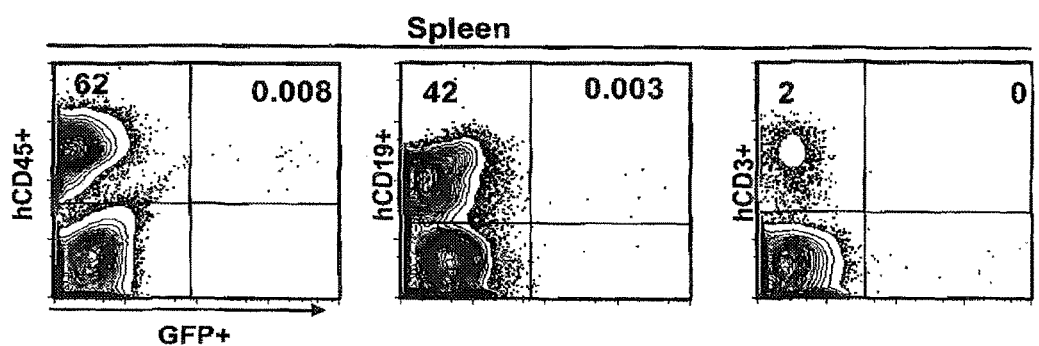
FIG. 9 represents the analysis by FACS of the transduction (GFP+) of human splenocytes (hCD45+), B-cells (hCD19+) and T-cells (hCD3+) in the spleen. The first histogram shows the results obtained with cells sorted according to hCD45 expression (hCD45+, vertical axis) and GFP expression (GFP+, horizontal axis). The second histogram shows the results obtained with cells sorted according to hCD19 expression (hCD19+, vertical axis) and GFP expression (horizontal axis). The third histogram shows the results obtained with cells sorted according to hCD3 expression (hCD3+, vertical axis) and GFP expression (horizontal axis).

Of utmost importance, the inventors verified in vivo escape of vectors by analysing transduction of the other hematopoietic tissues. They did not detect GFP$^+$ human thymocytes (FIG. 7), nor transduction of human CD19$^+$ B-cells and CD3$^+$ T-cells in the blood stream of these intrafemural injected mice (FIG. 8). Additionally, they did not detect significant levels of transduced B-cells (hCD19$^+$ cells) and transduced T-cells in the spleen (FIG. 9).

Summarizing, local administration of low doses of RDTR/SCFHA LV into the BM of humanized mice resulted in a selective transduction of hCD34$^+$ cells in vivo.

Sequence Identifiers Reference Table:

| SEQ ID NO: | Feature |
| --- | --- |
| 1 | Nucleic acid encoding a fusion of the transmembrane and extracellular domains of the feline endogenous RD114 virus envelope glycoprotein and the cytoplasmic domain of MLV-A envelope glycoprotein |
| 2 | Fusion of the transmembrane and extracellular domains of the feline endogenous RD114 virus envelope glycoprotein and the cytoplasmic domain of MLV-A envelope glycoprotein |
| 3 | Nucleic acid encoding a fusion of the SCF cytokine, the N-terminal domain of an influenza virus hemagglutinin glycoprotein, and a signal peptide |
| 4 | Fusion of the SCF cytokine, the N-terminal domain of an influenza virus hemagglutinin glycoprotein, and a signal peptide |
| 5 | Transmembrane and extracellular domains of the feline endogenous RD114 virus envelope glycoprotein |
| 6 | Cytoplasmic domain of Murine Leukemia Virus-A envelope glycoprotein |
| 7 | Signal peptide of the Murine Leukemia Virus-A envelope glycoprotein |
| 8 | Human c-Kit receptor |
| 9 | Human SCF cytokine |
| 10 | N-terminal domain of the Fowl Plague Virus hemagglutinin |
| 11 | Plasmid encoding the fusion protein of SEQ ID NO: 2 |
| 12 | Plasmid encoding the fusion protein of SEQ ID NO: 4 |
| 13 | VSV-G envelope glycoprotein |
| 14 | Plasmid encoding VSV-G |
| 15 | Plasmid encoding TPOHA |

What is claimed is:

1. A vector particle capable of specifically transferring biological material into CD34+ cells, wherein said vector particle comprises at least:
   a first protein which comprises the transmembrane and extracellular domains of the feline endogenous RD114 virus envelope glycoprotein, and
   a second protein which comprises a fusion of the Stem Cell Factor (SCF) cytokine and the N-terminal domain of an hemagglutinin glycoprotein;
wherein the vector particle does not comprise the Vesicular Stomatitis Virus (VSV) G envelope glycoprotein.

2. The vector particle according to claim 1, wherein the vector particle is a lentiviral vector particle.

3. The vector particle according to claim 2, wherein the lentiviral vector particle is selected from the group consisting of HIV and SIV.

4. The vector particle according to claim 1, wherein the biological material is one or more nucleic acids.

5. The vector particle according to claim 1, wherein the first protein comprises or consists in a fusion of the transmembrane and extracellular domains of the feline endogenous RD114 virus envelope glycoprotein and the cytoplasmic domain of a retroviral envelope glycoprotein.

6. The vector particle according to claim 5, wherein the cytoplasmic domain of a retroviral envelope glycoprotein is that of Murine Leukemia Virus-A.

7. The vector particle according to claim 1, wherein the second protein comprises or consists in a fusion of a SCF cytokine and the N-terminal domain of an influenza virus hemagglutinin glycoprotein.

8. The vector particle according to claim 1, wherein the first and the second proteins are fused.

9. A method for preparing a vector particle as defined in claim 1, comprising transferring (i) a first nucleic acid comprising a sequence encoding a first protein as defined in claim 1, and (ii) a second nucleic acid comprising a sequence encoding a second protein as defined in claim 1, in a producer cell, and recovering the vector particle from said producer cell.

10. A medicament comprising a vector particle as defined in claim 1 as active ingredient.

11. A method of specifically transferring the biological material into CD34+ cells ex vivo comprising using, in the absence of Retronectin®, the vector particle as defined in claim 1 for specifically transferring the biological material into CD34+ cells ex vivo.

12. The method according to claim 11, wherein the cells are comprised in a blood sample.

13. A method for preparing CD34+ cells intended for treating an individual, wherein CD34+ cells to be administered to the individual are contacted with a vector particle as defined in claim 1 in the absence of Retronectin®.

14. The method according to claim 13, wherein the cells are comprised in a blood sample.

15. The method according to claim 13, wherein the cells are transduced by one or more nucleic acids transferred from the vector particle.

* * * * *